United States Patent
Banin et al.

(10) Patent No.: US 11,193,034 B2
(45) Date of Patent: Dec. 7, 2021

(54) HYBRID NANOPARTICLES AS PHOTOINITIATORS

(71) Applicant: Yissum Research Development Company of the Hebrew University of Jerusalem Ltd., Jerusalem (IL)

(72) Inventors: Uri Banin, Mevasseret Zion (IL); Hermona Soreq, Jerusalem (IL); Shlomo Magdassi, Jerusalem (IL); Nir Waiskopf, Jerusalem (IL); Yuval Ben-Shahar, Jerusalem (IL); Amol Ashok Pawar, Jerusalem (IL); Shira Halivni, North Yehuda (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 0 days.

(21) Appl. No.: 16/552,429

(22) Filed: Aug. 27, 2019

(65) Prior Publication Data

US 2019/0390077 A1    Dec. 26, 2019

Related U.S. Application Data

(62) Division of application No. 15/740,869, filed as application No. PCT/IL2016/050693 on Jun. 29, 2016, now Pat. No. 10,442,944.

(Continued)

(51) Int. Cl.
| | |
|---|---|
| *C09D 11/101* | (2014.01) |
| *C09D 11/38* | (2014.01) |
| *B82Y 30/00* | (2011.01) |
| *G03F 7/00* | (2006.01) |
| *G03F 7/029* | (2006.01) |

(Continued)

(52) U.S. Cl.
CPC ............. *C09D 11/38* (2013.01); *A61K 6/17* (2020.01); *A61K 6/62* (2020.01); *A61K 6/71* (2020.01); *A61K 6/887* (2020.01); *B33Y 70/00* (2014.12); *C09D 11/101* (2013.01);
(Continued)

(58) Field of Classification Search
CPC ........ C09D 11/38; C09D 11/101; A61K 6/17; A61K 6/62; A61K 6/71; A61K 6/887; B33Y 70/00; B33Y 70/10; G03F 7/0037; G03F 7/029; B82Y 30/00
See application file for complete search history.

(56) References Cited

U.S. PATENT DOCUMENTS

| | | |
|---|---|---|
| 2014/0275319 A1 | 9/2014 | Yamada et al. |
| 2015/0075397 A1* | 3/2015 | Gresty .............. B41F 16/00 101/129 |

FOREIGN PATENT DOCUMENTS

| | | |
|---|---|---|
| KR | 10-2013-0113770 A | 10/2013 |
| WO | 2005/075339 A2 | 8/2005 |

(Continued)

OTHER PUBLICATIONS

Banin et al., "Hybrid Semiconductor—Metal Nanoparticles: From Architecture to Function", Chem. Mater., vol. 26, pp. 97-110, (2014).

(Continued)

*Primary Examiner* — Yaovi M Ameh
(74) *Attorney, Agent, or Firm* — Vorys, Sater, Seymour and Pease LLP; Anthony Venturino

(57) ABSTRACT

Provided is a novel photoinitiator in the form of a hybrid nanoparticle constructed of a semiconductor and metallic regions, and uses thereof.

14 Claims, 15 Drawing Sheets

Related U.S. Application Data

(60) Provisional application No. 62/185,821, filed on Jun. 29, 2015, provisional application No. 62/343,091, filed on May 30, 2016.

(51) Int. Cl.
  *B33Y 70/00* (2020.01)
  *A61K 6/17* (2020.01)
  *A61K 6/62* (2020.01)
  *A61K 6/71* (2020.01)
  *A61K 6/887* (2020.01)

(52) U.S. Cl.
  CPC ............ *G03F 7/0037* (2013.01); *G03F 7/029* (2013.01); *B82Y 30/00* (2013.01)

(56) References Cited

FOREIGN PATENT DOCUMENTS

| WO | 2008/102351 A2 | 8/2008 |
|---|---|---|
| WO | 2011/141917 A2 | 11/2011 |
| WO | 2013/132491 A2 | 9/2013 |

OTHER PUBLICATIONS

Costi et al., "Visible Light-Induced Charge Retention and Photocatalysis with Hybrid CdSe—Au Nanodumbbells", Nano Letters, vol. 8, No. 2, pp. 637-641, (2008).

Fruk et al., "Light-Induced Triggering of Peroxidase Activity Using Quantum Dots", ChemBioChem, vol. 8, pp. 2195-2198, (2007).

Gruber, "Photoinitiators for Free Radical Polymerization", Prog. Polym. Sci., vol. 17, pp. 953-1044, (1992).

Guo et al., "Aliphatic ketones and aldehydes as water-soluble photoinitiators for the photopolymerization of methacrylic acid", Polymer, vol. 54, pp. 4940-4947, (2013).

Ipe et al., "On the Generation of Free Radical Species from Quantum Dots", Small, vol. 1, No. 7, pp. 706-709, (2005).

Kang et al., Kinetics of Acrylamide Solution Polymerization Using Potassium Persulfate as an Initiator by in situ IR, Macromolecular Research, vol. 12, No. 1, pp. 107-111, (2004).

Mokari et al., "Selective Growth of Metal Tips onto Semiconductor Quantum Rods and Tetrapods", SCIENCE, vol. 304, pp. 1787-1790, (2004).

Rajendran et al., "Photocatalytic activity of colloidal CdS nanoparticles with different capping ligands", J. Mater. Chem., vol. 19, pp. 6348-6353, (2009).

Rajendran et al., "Photocatalytic Activity of Protein-Conjugated CdS Nanoparticles", Small, vol. 6, No. 18, pp. 2035-2040, (2010).

Tehfe et al., "Photopolymerization Reactions: On the Way to a Green and Sustainable Chemistry", Appl. Sci., vol. 3, pp. 490-514, (2013).

Yagci et al., "Photoinitiated Polymerization: Advances, Challenges, and Opportunities", Macromolecules, vol. 43, pp. 6245-6260, (2010).

\* cited by examiner

Figure 5A
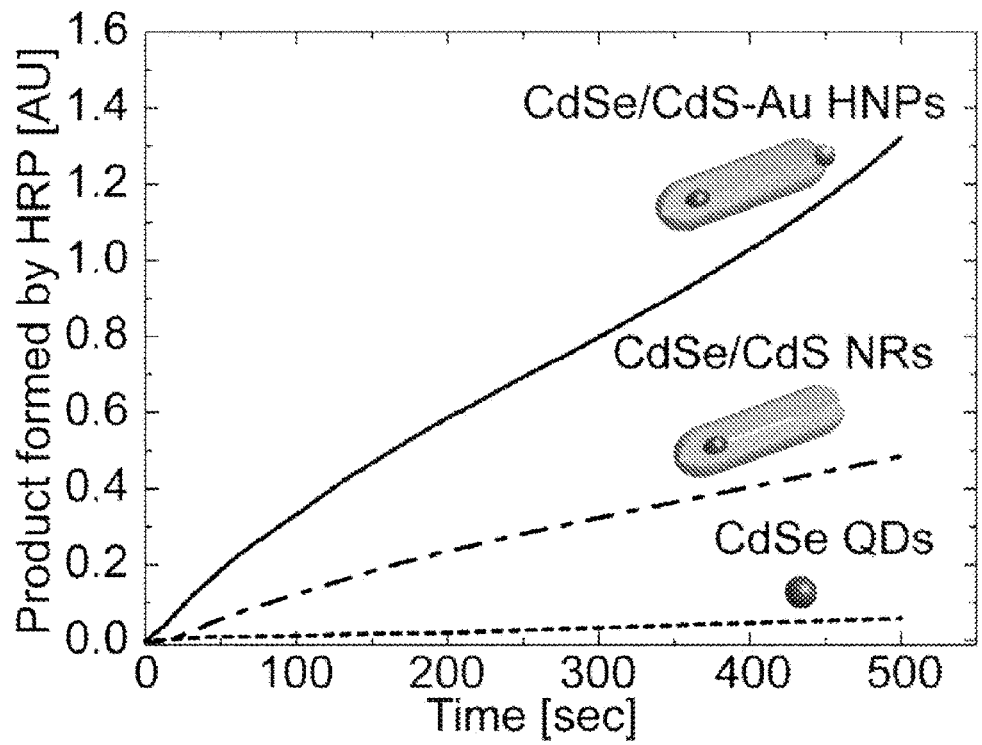
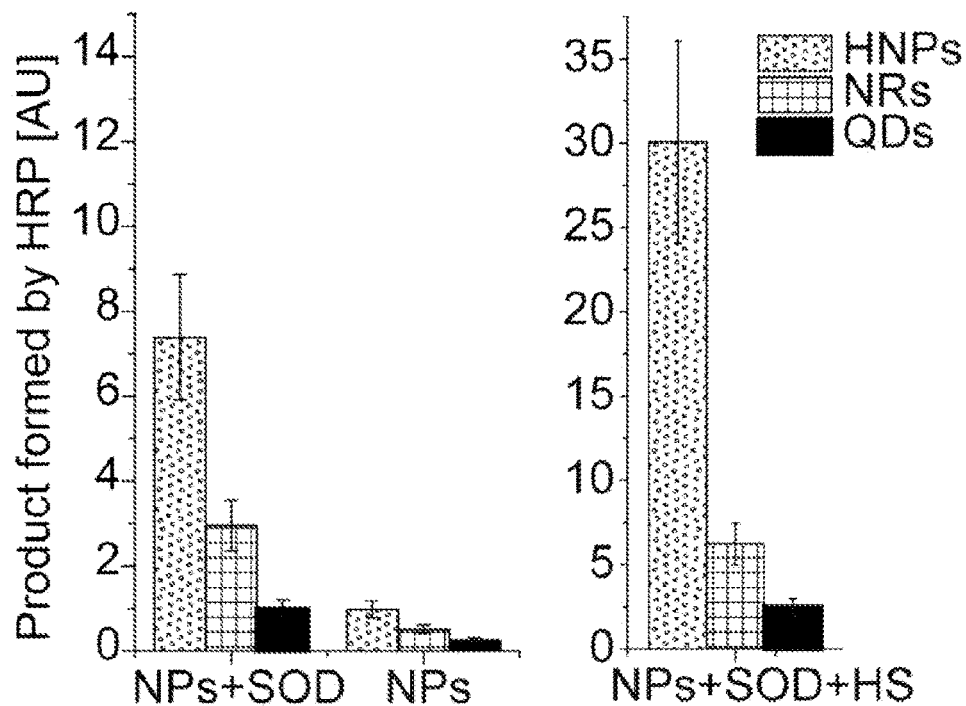
Figure 5B
Figure 5C

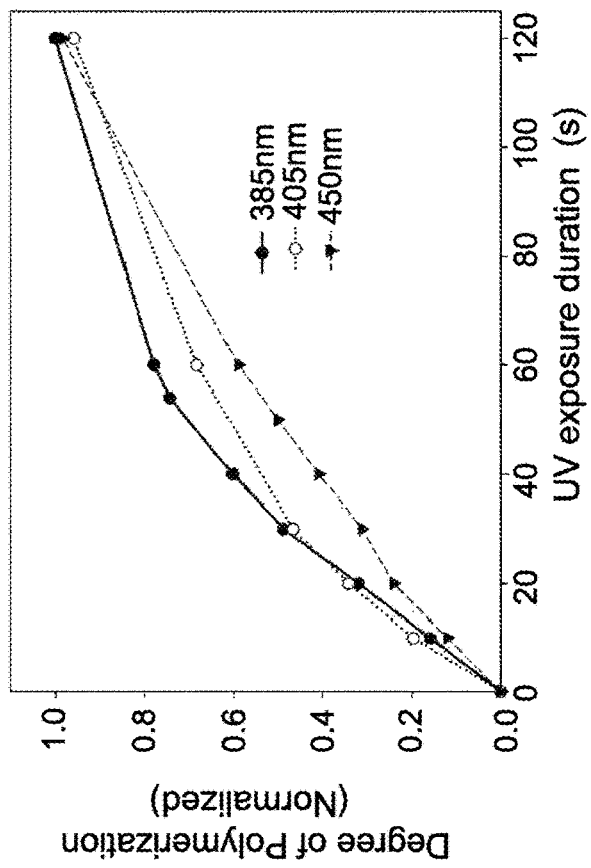
Figure 14C
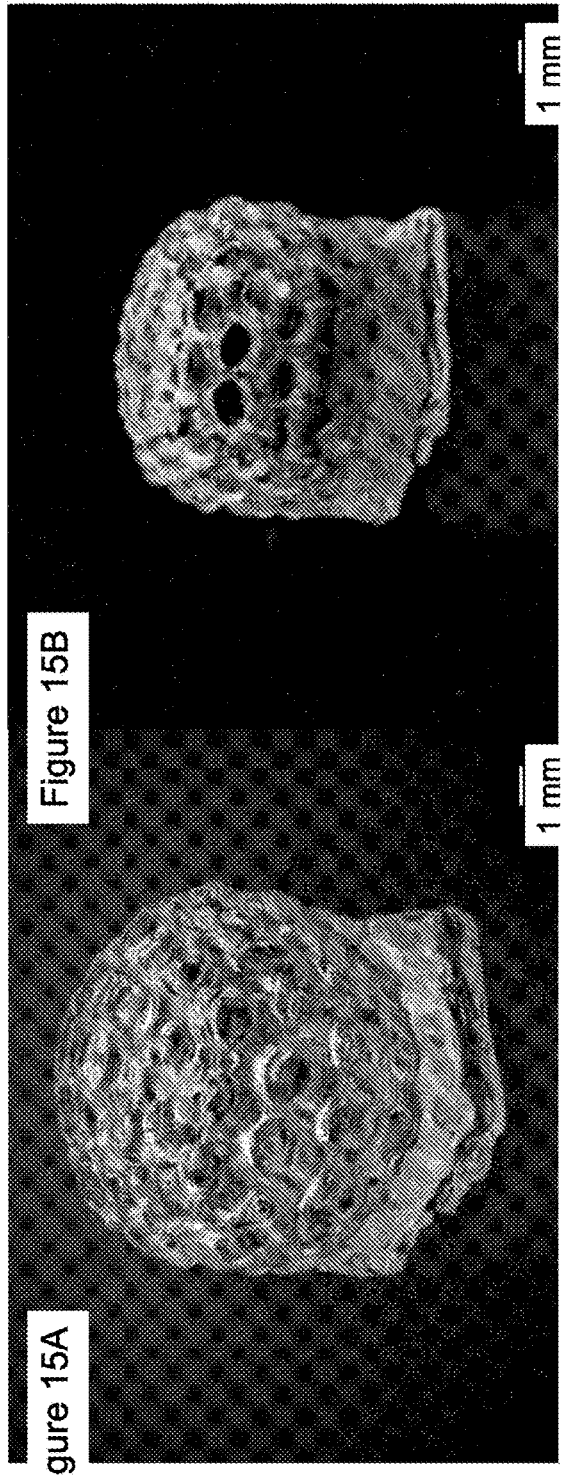
Figure 15A
Figure 15B

Before polymerization

After polymerization

HYBRID NANOPARTICLES AS PHOTOINITIATORS

TECHNOLOGICAL FIELD

The invention disclosed herein generally concerns photoinitiators in the form of hybrid nanoparticles and uses thereof.

BACKGROUND

Semiconductor-metal hybrid nanoparticles (HNPs) manifest efficient light-induced charge separation [1-10]. Upon light excitation, the semiconductor component generates an electron-hole pair (exciton), followed by electron charge transfer to the metal domain, due to energy band alignment of the semiconductor-metal nanojunction. This, combined with the known catalytic characteristics of metal nanocrystals, made the HNPs leading candidates as photocatalysts for energy and environmental applications. In particular, HNPs were investigated as photocatalysts in water splitting for hydrogen generation under light irradiation, as means of directly converting solar energy to chemical energy stored in a fuel. Within these experiments, HNPs showed efficient hydrogen generation, whereas semiconductor nanocrystals have shown negligible activity.

Another photocatalytic application is the photo-reduction of carbon dioxide, using solar energy for promoting the reduction of green-house gas contents along with alternative sustainable avenues for production of methane and other hydrocarbon fuels.

Semiconductor nanocrystals have also been investigated for their use in diverse bioimaging and sensing applications, where they showed profound advantages over organic dyes and fluorescent proteins; mainly in terms of wavelength tunability, light sensitivity, and photochemical stability. Moreover, they have been suggested for photodynamic therapy and as light activated modulators of biological functions in neuronal stimulation applications, serving as alternatives to other approaches utilizing small molecule photoswitches, caged molecules enabling photorelease and opto-genetics tools.

Previous reports have shown that in the presence of oxygen, light excitation of semiconductor nanocrystals can result in the formation of reactive oxygen species (ROS) [11, 12]. The amount and type of ROS was found to depend on the composition and surface coating of the nanocrystals. Moreover, it was suggested that the produced ROS can be used to activate enzymes such as horseradish peroxidase (HRP) [13, 14]. This would depend on reduction of molecular oxygen with two protons and two electrons transferred from the conduction band of the semiconductor nanocrystals.

REFERENCES

[1] T. Mokari, E. Rothenberg, I. Popov, R. Costi, U. Banin, Selective growth of metal tips onto semiconductor quantum rods and tetrapods. *Science* 304, 1787 (2004).
[2] R. Costi, A. E. Saunders, E. Elmalem, A. Salant, U. Banin, Visible light-induced charge retention and photocatalysis with hybrid CdSe—Au nanodumbbells. *Nano Lett* 8, 637 (2008).
[3] U. Banin, Y. Ben-Shahar, K. Vinokurov, Hybrid Semiconductor-Metal Nanoparticles: From Architecture to Function. *Chem. Mater.* 26, 97 (2014).
[4] Y. Yagci, S. Jockusch, N. J. Turro, Photoinitiated Polymerization: Advances, Challenges, and Opportunities. *Macromolecules* 43, 6245 (2010).
[5] R. Guo, Y. Gao, M. Wu, H. Wang, Aliphatic ketones and aldehydes as water-soluble photoinitiators for the photopolymerization of methacrylic acid. *Polymer* 54, 4940 (2013).
[6] H. F. Gruber, Photoinitiators for Free-Radical Polymerization. *Prog Polym Sci* 17, 953 (1992).
[7] M. A. Tehfe, F. Louradour, J. Lalevee, J. P. Fouassier, Photopolymerization Reactions: On the Way to a Green and Sustainable Chemistry. *Appl Sci-Basel* 3, 490 (2013).
[8] S. C. Kang, Y. J. Choi, H. Z. Kim, J. B. Kyong, D. K. Kim, Kinetics of acrylamide solution polymerization using potassium persulfate as an initiator by in situ IR. *Macromol Res* 12, 107 (2004).
[9] WO2008/102351.
[10] WO2005/075339.
[11] Ipe, B. I.; Lehnig, M.; Niemeyer, C. M. *Small* 1, 706-709 (2005).
[12] Rajendran, V.; Lehnig, M.; Niemeyer, C. M. *J Mater Chem* 19, 6348-6353 (2009).
[13] Rajendran, V.; Konig, A.; Rabe, K. S.; Niemeyer, C. M. *Small* 6, 2035-2040 (2010).
[14] Fruk, L.; Rajendran, V.; Spengler, M.; Niemeyer, C. M. *Chembiochem* 8, 2195-2198 (2007).

SUMMARY OF THE INVENTION

Herein, the inventors introduce, for the first time, use of visible band-gap semiconductor-metal hybrid nanoparticles (HNPs) as photo-catalysts for generating reactive species, in form of peroxides and radicals, a key step toward establishing their function in modulating a variety of chemical and/or biological reactions by light.

The inventors have demonstrated that unlike systems, which are not HNPs and which show relatively limited efficiency for production of radicals and peroxides, the HNPs utilized in accordance with the invention, are highly efficient in the production of such reactive species. Without wishing to be bound by theory, it is believed that the low efficiency associated with non-HNPs results from their inherently low efficiency of charge transfer due to strong competing decay pathways, such as electron-hole recombination, along with oxidation and etching of the semiconductor nanocrystals surface.

Thus, in a first aspect, the invention provides a tool for generating reactive species, such as radicals and peroxides, in solution, the tool being in the form of a plurality of HNPs. The synthetic tool may thus be utilized in a radical- and/or peroxide-assisted conversion of a multitude of chemical and biological reactions by exposure to light. The reactivity of the HNPs is not limited in any way to one particular set of conditions, but rather finds utility and usefulness in a variety of applications which employ various and different conditions, such as, inter alia, temperatures, pressures, concentrations, light intensities, duration of exposure, matrix, etc.

The reactive species formed in the presence of the HNPs, and under conditions of illumination, are typically radical species, in the form of an atom or group of atoms that have one or more unpaired electrons. The radicals may be derived from any atom, such as oxygen, sulfur, carbon and hydrogen atoms, or from any group of atoms containing at least one such atom. Other atom radicals may be similarly suitable.

When the radicals are derived from oxygen atoms, reactive oxygen species (ROS) are obtained. The ROS species may be in a variety of forms, or mixtures of such forms, e.g., in the form of a superoxide anion, as peroxide, a hydroxyl radical and mixtures thereof.

The reactive species may be formed by irradiating a medium, either liquid or solid, comprising the HNPs and at least one material capable of radical formation. The medium may be a solid or liquid formulation, a liquid suspension, a liquid dispersion or any solid material comprising the above recited components. The material capable of radical formation may be any material which is capable of accepting at least one unpaired charge from the HNPs or from any other formed reactive species, or which dissociates into a reactive species in the presence of the HNPs and upon suitable irradiation by light. The at least one material may thus be selected amongst any material, such as atoms, ions and molecules (compounds). Suitable exemplary molecules may be water, a hydroxide-containing molecule, oxygen, a peroxide, azo compounds, disulphides, persulfates, carbon dioxide, carbonate, azide, ammonia, hydroxylamine, nitrogen dioxide, nitrogen trioxide (e.g. nitrate and nitric acid), phosphite, phosphate, sulfur dioxide, sulphite, sulfate, peroxomonosulfate, selenite, dithiocyanate, dihalogen, chlorine and bromine dioxide, compounds or molecules which possess at least one such group, and others.

Once the reactive species is formed, as a relatively unstable species, it may react with an additional material in its vicinity to cause or bring about modulation of the material's structure, function or reactivity. The modulation may be detected, analysed, quantified and may be utilized for any purpose, e.g., diagnostic, physical, chemical or biological.

In some embodiments, the material capable of radical formation is the same or different than the additional material which is susceptible to modulation.

Thus, in another aspect, the invention contemplates a novel photo-initiator in the form of a hybrid nanoparticle (HNP), as herein defined.

The invention further provides a formulation comprising HNPs and at least one material capable of being (catalytically) transformed; namely transformed (structurally and/or functionally) in the presence of the HNPs and under suitable light irradiation into a material which is different (structurally and/or functionally) from the starting material and which may optionally cause transformation (structurally and/or functionally) of a further material present in the formulation. The material which is capable of being transformed may be the material susceptible for radical formation or the material interacting with the reactive species formed.

As used herein, the HNPs utilized according to the invention are nanoparticles, each comprising at least one metal/metal alloy region and at least one semiconductor region. The nanoparticles are selected to be capable, upon light irradiation by visible and/or near IR range and/or UV range light, at a suitable wavelength, of forming reactive species in a medium.

The nanoparticles may be of any shape and size and may comprise any number of metal/metal alloy regions and any number of semiconductor regions. In some embodiments, the nanoparticles comprise at least one or at least two metal/metal alloy regions, separated by at least one semiconductor region, wherein each of said at least two metal/metal alloy regions is of a different or same metal/metal alloy material.

The different metal/metal alloy regions and different semiconductor regions may be of the same or different materials (same or different metals or metal alloys; same or different semiconductor materials), as selected herein.

In some embodiments, at least a portion of the HNPs population utilized in a certain reaction or application, or all of the HNPs in said population is in the form of nanodumbells. In some embodiments, at least a portion of the HNPs population utilized in a certain reaction or application is in the form of nanodumbells. In some embodiments, all HNPs utilized in a certain reaction or application are in the form of nanodumbells. In some embodiments, the nanodumbells are disclosed in WO 05/075339 or in any application derived therefore, herein incorporated by reference.

The HNPs population (being formed of a plurality of one or more nanoparticle of the same or different shape and/or material) may comprise a blend of nanoparticles tuned to match specific or broad range optical properties of a material. Such blending of the nanoparticle population permits tuning of the energy levels and thus the redox potential of the nanostructures.

In some embodiments, the HNPs have at least one elongated structure element comprising a first material, bearing on at least one end portion thereof a second material selected from metal and metal alloy. The first and second materials differ in their electrical conductivity and/or chemical reactivity and/or composition. In some embodiments, the elongated structure element comprises of semiconductor material(s).

In some embodiments, the HNPs are selected amongst seeded elongated elements (e.g., seeded rod), bearing on at least one end portion thereof a material selected from metal and metal alloy. In some embodiments, the seeded elongated elements comprise at least one semiconductor material.

The HNPs constructed as defined and exemplified herein may be made of any metal, metal alloy or semiconductor solid substance. The first material is selected from semiconductor materials, insulating materials, metals and mixtures thereof. In some embodiments, the first material is a semiconductor material selected from such materials known in the art. In some embodiments, the semiconductor material is selected from Group II-VI semiconductors, Group III-V semiconductors, Group IV-VI semiconductors, Group IV semiconductors, Group III-VI semiconductors, Group I-VI semiconductors, ternary semiconductors, and alloys of any of the above semiconductors; or as combinations of the semiconductors in composite structures and core/shell structures.

In some embodiments, the HNPs are made from Group II-VI semiconductors, alloys made therefrom and core/shell structures made therefrom. Specific examples of Group II-VI semiconductors include CdSe, CdS, CdTe, ZnSe, ZnS, ZnTe, ZnO, HgS, HgSe, HgTe and alloys thereof, e.g., CdZnSe, combinations thereof and core/shell layered-structures thereof.

Specific examples of Group III-V semiconductors include InAs, InP, GaAs, GaP, InN, GaN, InSb, GaSb, AlP, AlAs, AlSb and alloys thereof, e.g., InAsP, CdSeTe, ZnCdSe, InGaAs and the like.

Group IV-VI semiconductors may be selected from PbSe, PbTe and PbS and alloys thereof and Group IV semiconductors may be selected from Si and Ge and alloys thereof.

In some embodiments, the semiconductor may be selected from $Sn_2S_6$, $Sn_2Se_6$, $In_2Se_4$, $In_2Te_3$, $Ga_2Se_3$, $CuInSe_2$, $Cu_7S_4$, $Sb_2Te_3$, ZnS, ZnSe, ZnTe, AgS, AgSe, AgTe, $Cu_2S$, $Cu_2Se$, $CuInS_2$, ZnS, ZnSe and ZnTe.

In some embodiments, the semiconductor is ZnO, ZnS, ZnSe or ZnTe.

In some embodiments, the semiconductor is ZnO. In some embodiments, the ZnO nanoparticles are decorated with multiple metal islands, ZnSe—Au nano-frames, and others.

Additionally, combinations of the above in composite structures constructed of sections with different semiconductor materials, for example CdSe/CdS or any other combinations, as well as core/shell structures of different semiconductors such as for example CdSe/ZnS core/shell nanorods, are also within the scope of the present invention.

In some embodiments, the HNPs do not comprise Cd.

In some embodiments, the HNPs are selected to comprise non-toxic semiconductor materials.

The first material, being in some embodiments a semiconductor, is different than the second material in at least one property selected from electrical conductivity, chemical reactivity and composition. Thus, in cases where the first material is a semiconductor material, the second material may be a metal, metal alloy, or an insulating material.

In some embodiments, the second material is at least one metal or a metal alloy. Examples of metals include transition metals such as Cu, Ag, Au, Pt, Co, Pd, Ni, Ru, Rh, Mn, Cr, Fe, Ti and alloys of such metals.

The HNPs may be of any shape. For certain applications, HNPs having elongated shape, for example rods, wires, or tubes are better suited. For other applications, branched forms may be better suited.

In some embodiments, the HNPs are in the form of nanorods, nanodumbells, having a diameter in the range of about 1 nm to about 100 nm, where the dimensions along the longest nanoparticle axis may range from about several nanometres to about 1 micrometer.

In some embodiments, at least one dimension (length or diameter or thickness) of the HNPs is in the range of 1 nm to 500 nm. In some embodiments, the metal region is of a size between 0.3 nm and 50 nm. In some embodiments, the HNPs are CdS—Au hybrid rods, wherein the CdS rods are of diameters of between 1-20 nm, lengths of 7-500 nm, and contain a single Au tip at one of their apexes being about 2 nm in diameter.

In some embodiments, the HNPs are selected from various semiconductor materials, as recited herein.

In some embodiments, the semiconductor material is selected from II-VI semiconductors, e.g., CdSe, CdS, CdTe, ZnS, ZnSe, ZnS and alloys thereof; III-V semiconductors such as InP, GaP, InAs and alloys thereof; copper chalcogenides including $Cu_2S$, $Cu_2Se$ and oxides such as $Cu_2O$, ZnO; the semiconductor material occupying or being or taking on a shape such as a dot, a rod, a platelet, a tetrapod, a frame, and the at least one metal region being of a metallic material, for example Au, Ag, Pt, Ni and other metals or metal oxides.

The HNPs may additionally or alternatively be selected to exhibit tunable high absorption extinction coefficients in a desired spectral regime, e.g., UV-blue region, which can also be tailored to cover, e.g., the visible range via proper tuning of the composition size, shape and structure. For example, CdS—Au rods as demonstrated herein have a high absorption extinction coefficient value, epsilon, of $1.17 \times 10^7$ $M^{-1}$ $cm^{-1}$, $1.08 \times 10^7$ $M^{-1}$ $cm^{-1}$ and $9.66 \times 10^6$ $M^{-1}$ $cm^{-1}$ at 385 nm, 405 nm and 450 nm, respectively. High performance photo-polymerization specifically in the near UV-visible range of 300-700 nm, or in the range of 385-450 nm is therefore also possible with photo-initiators according to the invention.

The HPNs are light activated hybrid nanoparticles when irradiated by UV light at between 200 and 400 nm, and/or near UV light at between 300 and 400 nm, and/or visible light at between 400 and 700 nm, and/or near Infrared (NIR) light at between 0.7 and 1.4 μm. In some embodiments, the HPNs are light activated at a spectral regime of 200 to 400 nm and/or 300 to 400 nm and/or 400 to 700 nm and/or 0.7 to 1 μm and/or near Infrared (NIR) 0.7 to 1.4 μm.

The HNPs are not consumed during the polymerization reaction and therefore act as catalysts and further do not decompose essentially upon irradiation, thus impose no harmful by-products.

The invention further provides a kit comprising:
a plurality of HNPs;
a medium for carrying out a diagnostic analysis for determining the presence or absence of at least one material; or for carrying out a synthetic transformation of at least one material, and
instructions of carrying out said analysis and/or synthetic transformation under exposure to light.

The invention further provides a diagnostic method for detecting presence or activity (e.g., enzymatic activity) of a biological material, the method comprising irradiating a medium comprising HNPs, optionally at least one material capable of radical formation, and at least one biological material susceptible of (photocatalytic) conversation, and analyzing the resulting product, wherein the presence and/or identity and/or quantity of said product permits diagnosis.

The invention further provides a biological assay comprising at least one photo-initiator according to the invention, optionally at least one material capable of radical formation, and at least one biological material susceptible of (photocatalytic) conversation.

The invention further provides use of a plurality of HNPs in a method for directly or indirectly catalyzing, e.g., photocatalyzing, conversion of at least one material in a medium.

The invention further provides a method for generating a reactive species in a form of a radical or peroxide in a medium, the process comprising irradiating a medium comprising HNPs and at least one material susceptible of conversation (e.g., photocatalytic conversion).

The invention further provides use of HNPs as active materials in a method of controlling, modulating or generally affecting biological processes through illumination.

The invention further provides use of HNPs in a method for modulating enzyme property and/or activity and for affecting biological pathways through radicals and/or peroxides formation. As used herein, the term "modulating enzyme property" refers to the ability to change an enzyme's property, structure, function or activity by exposing the enzyme to a reactive species, e.g., radical or peroxide. The modulation may be for diagnostic purposes or for the purpose of achieving a new or modified product via such radical- or peroxide-mediated process.

The invention further provides a medium or formulation or a solution comprising an enzyme and a plurality of HNPs.

As known in the art, radicals and peroxides are often considered as toxic entities that may induce significant damage and even result in cells death. However, their controlled production is required in numerous assays and biological functions. For example, HRP uses $H_2O_2$ as a substrate and is widely employed in standard assays for detection and quantification of proteins, such as in enzyme-linked immunosorbent assay, immune histochemistry, quantification after gel electrophoresis and as signal amplifier in various sensors. Furthermore, diverse biological pathways, including metabolic and immune reactions include and depend on $H_2O_2$.

Thyroid peroxidase (TPO) depends on $H_2O_2$ for the production of the thyroid hormones including thyroxine (T4) and triiodothyronine (T3). Interference with TPO activity may lead to the autoimmune disease Hashimoto's thyroiditis, resulting in fatigue, joint and muscle pain, depression, and more.

In addition, potent antiparasite enzymes of the immune system, including myeloperoxidase, eosinophil peroxidase, and lacto-peroxidase use $H_2O_2$ in their fight against pathogens. The ability to induce such activities on demand by optical modulation has a potential value for biological research and biomedical applications.

Using the metal-tipped semiconductor nanorod HNPs (such as those disclosed in WO 05/075339 or in any application derived therefore, herein incorporated by reference) as model systems, light-induced ROS formation was observed and characterized through combination of spectroscopic assays, polarography and electron paramagnetic resonance (EPR). Hydrogen peroxide, super-oxide, and hydroxyl radicals were detected and the photocatalytic activity of the hybrid nanoparticles was found to be conspicuously improved over that of the semiconductor nanocrystals. This photocatalytic functionality was used for modulation of horseradish peroxidase enzymatic activity as a model system, demonstrating the potential use of hybrid nanoparticles as active agents to control biological processes through illumination.

In a model case, the HNP model system consisted of metal-tipped seeded CdSe/CdS—Au nanorods. The synthesis of the HNPs was carried out in consecutive steps, as disclosed, for example in WO 05/075339 or in any application derived therefore, herein incorporated by reference. First, CdSe/CdS seeded nanorods (NRs) were synthesized. Specifically, CdSe/CdS seeded NRs with a small CdSe seed (2.3 nm) leading to quasi type-II band alignment were prepared, as they offer improved charge separation compared to type I systems. Next, selective metal growth on the semiconductor nanorods apex was carried out under dark conditions and at room temperature. Phase transfer with polyethylenimine (PEI) was used to replace the original hydrophobic ligands and to achieve well-dispersed HNPs in aqueous solutions.

FIG. 1A (inset) presents the transmission electron micrograph (TEM) of the HNPs (see FIG. 2 for their size distribution histograms) showing their matchstick-like structure of 52±4 nm×4.4±0.4 nm CdSe/CdS NRs with single gold tips on the apex (stronger contrast, typically 1.6 nm in diameter). The spectra of both types of NPs exhibit a sharp rise at 480 nm, attributed to the CdS rod absorption onset (FIG. 1A). Note that the band gap of the seeded rod was at 560 nm (FIG. 3). Upon growth of the small Au tip, an increased absorption tail toward the red was observed.

Photoinduced modulation of peroxidases activity by HNPs was examined with HRP using an assay that catalyzes the production of quinoneimine dye in the presence of $H_2O_2$, 4-aminoantipyrine (4-AAP) and phenol (FIG. 4A). Excitation of the HNPs with a 405 nm 20 mW/cm$^2$ laser resulted in the formation of a new absorption peak at 495 nm, which was a signature of the formation of HRP products that significantly increased with irradiation time (FIG. 1B, inset). In addition, turning the illumination source on and off (grey and black arrows, respectively in FIG. 1B) resulted in a staircase behaviour, where the absorption increased only while the light was on, proving a photo-switching of HRP activity by excitation of the HNPs. Furthermore, control experiments without oxygen, light or HNPs did not cause significant absorption changes, confirming the central interrelated role of these three elements in product formation. Without HRP, some product formation was also detected (FIG. 4). Hence, to represent the net contribution of the HNPs to the effective enzyme action, this signal was subtracted from the kinetic data analyzed and presented.

The structural effect of the nanoparticles was first examined and compared on the efficiency of product formation, using solutions of CdSe quantum dots (QDs), CdSe/CdS seeded NRs, and CdSe/CdS—Au HNPs with similar optical density at the excitation wavelength of 405 nm. In this manner, a total apparent efficiency comparison was conducted between the different types of nanosystems. The capacity of each type of NPs to stimulate HRP activity was examined with and without the addition of hole acceptor and SOD. FIG. 5A shows that HNPs excitation in the presence of hole acceptor and superoxide dismutase (SOD) results in 3 times faster kinetics and final product concentration as compared to the excitation of bare NRs, showing a clear superiority for the use of HNPs for applications requiring $H_2O_2$. In comparison, CdSe quantum dots showed a rather limited capacity to produce $H_2O_2$, due to alternative charge recombination processes in the absence of effective electron-hole charge separation in the small volume QD. Moreover, given the same optical density used in the experiments and the smaller molar extinction coefficient of the CdSe QDs relative to the NRs and HNPs, the actual concentrations of the QDs were significantly higher and yet HNPs revealed the higher efficiency.

Importantly, light excitation of 5 nm gold nanoparticles did not show any product formation, supporting the hypothesis that the higher product formation resulted from the synergistic light-induced charge separation phenomenon across the semi-conductor-metal nanojunction. Similar behaviour was also observed when comparing CdS NRs and CdS—Au HNPs (FIG. 2 and FIG. 6). This further substantiated the advantage of the use of HNPs over CdS QDs. The inherent small capacities of the nanoparticles without hole acceptor and SOD to produce $H_2O_2$ showed a similar trend, HNPs>NRs>CdSe QDs (FIG. 5B and FIG. 6). The addition of SOD, which was used by cells to transform superoxide radicals to $H_2O_2$, resulted in about 7-fold increase in product formation in comparison to the native capacities (FIG. 5B). The enhancement of the signal by SOD provides direct evidence for the formation of superoxide radicals by the HNPs, which then contribute to the overall $H_2O_2$ generation. This also provides another example for activation of enzymatic activity by light-induced ROS formation using HNPs.

Ethanol, although not biologically relevant and not the best sacrificial hole acceptor, was selected for this study, due to minimal interference to the used characterization assays. The addition of ethanol resulted in faster kinetics for both the HNPs and NRs systems (FIG. 5C). Notably, although the addition of hole acceptor affected both systems, its effect on the HNPs efficiency was found to be much more pronounced. Moreover, while in experiments without ethanol the activity was reduced with the irradiation time until a plateau was seen (FIG. 4), the addition of ethanol yielded longer sustained activity and stability. These observations are compatible with the notion that sacrificial hole acceptors enhance the photocatalytic performance and prolong the stability of HNPs by minimizing the probability for electron-hole recombination and photo-oxidation of their semiconductor component.

To investigate the mechanism of the ROS formation by HNPs, the kinetics of soluble molecular oxygen consumption under illumination was studied as well. FIG. 7A presents normalized kinetic measurements of oxygen consumption in a closed cell as measured by polarography at isothermal conditions. HNPs-PEI presented a considerably higher rate of oxygen consumption, 1.7 μmol L$^{-1}$ sec$^{-1}$, compared to the rate of bare NRs-PEI, 0.8 µmol L$^{-1}$ sec$^{-1}$. This rate is consistent with and similar to the rate of HRP product formation (0.6 µmol L$^{-1}$ sec$^{-1}$), suggesting that the formation of H$_2$O$_2$ and superoxide are the dominant processes.

The formation of additional possible radicals was measured either via fluorescence assay or directly by electron paramagnetic resonance spectroscopy (EPR). FIG. 7B shows kinetic measurements of hydroxyl radicals production by HNPs and NRs by a fluorescence assay. Nanoparticles were excited in the presence of the hydroxyl radical indicator, terephthalic acid (TPA), which reacted to produce 2-hydroxyterephthalic acid (HTA). The latter had a distinctive emission peak at 425 nm upon 310 nm excitation (inset). Superior hydroxyl radical formation was observed when stimulating the HNPs in comparison to the bare NRs (FIG. 7B). The observed higher formation of hydroxyl radicals could originate from either the excited holes in the semiconductor valence band or by decomposition of H$_2$O$_2$. This was in line with more efficient charge separation in the HNPs and further demonstrated that the hybrids can be applied to achieve efficient and controlled production of hydroxyl radicals. For both systems, the addition of ethanol suppressed HTA production. This may result from dual functioning of ethanol, both as a hole acceptor and as a hydroxyl radical scavenger.

Hydroxyl radicals may contribute to unspecific effects on biological systems and can also rapidly attack the superoxide radicals. It was surmised that this might somewhat limit the effect of added SOD in the case of HRP activation, and hypothesized that adding a sacrificial hole acceptor would increase both the efficiency and the specificity of the system. EPR measurements on both HNPs and NRs in phosphate buffered saline, using 5,5-dimethyl-pyrroline N-oxide (DMPO) as the radical trapping agent and the following theoretical simulations are presented in FIG. 7C (further experimental and model details are summarized in Table 1 and Table 2).

TABLE 1

Area quantification results (in percent) for the formation of different ROS following visible light excitation of NPs coated by PEI, with and without ethanol. All samples showed 3% of a non-specific signal.

| Nanoparticle type | Ethanol | *OH | *OOH | *SO$_3^-$ | CH$_3$C•HOH | Correlation |
|---|---|---|---|---|---|---|
| CdSe/CdS NRs | − | 3% | 94% | — | — | 0.94 |
| CdSe/CdS NRs | + | — | 94% | — | 3% | 0.95 |
| CdSe/CdS—Au HNPs | − | 31% | 54% | 12% | — | 0.93 |
| CdSe/CdS—Au HNPs | + | 15% | 50% | 16% | 16% | 0.9 |

TABLE 2

Simulation parameters used for EPR measurements (DMPO radical trapping agent) with comparison to relevant literature parameters.

| Radicals | A$_N$/G | A$_H$/G | Additional A$_H$/G |
|---|---|---|---|
| Simulation parameters ||||
| •OH | 15 | 15 | |
| •OOH | 14.1 | 11.3 | 1.25 |
| CH$_3$C*HOH | 15.8 | 22.8 | |
| SO$_3$•$^-$ | 14.4 | 15.9 | |
| Unspecific signal | 14.5 | | |

TABLE 2-continued

Simulation parameters used for EPR measurements (DMPO radical trapping agent) with comparison to relevant literature parameters.

| Radicals | A$_N$/G | A$_H$/G | Additional A$_H$/G |
|---|---|---|---|
| Literature ||||
| •OH | 14.77-15.2 | 14.77-15.2 | |
| •OOH | 14.1-14.3 | 11.3-11.7 | 1.25 |
| CH$_3$C*HOH | 15.8 | 22.8 | |
| SO$_3$•$^-$ | 14.4-14.7 | 15.9-16.5 | |

Both systems showed a strong signal of DMPO-OOH with hyperfine coupling of aN=14.1G, aH=11.3G, and aH=1.25G that supports the observation of significant superoxide production triggered by light excitation. However, in the NR system this signal accounted to more than 90% of the total signal, whereas its contribution in the case of the HNPs was only 50%. In the hybrid system, a second strong signal of DMPO-OH was found with a hyperfine coupling of aN=aH=15G, suggesting that the HNPs also produce significant amounts of hydroxyl radicals. This observation was compatible with the observations of the fluorescence assay for hydroxyl radical formation and was confirmed by the addition of ethanol, which as noted above can trap hydroxyl radicals. Ethanol addition yielded a third radical specie with hyperfine coupling of aN=15.8G and aH=22.8G, which indicated the presence of CH$_3$C*HOH, an ethanol-derived radical adduct (Table 1 and FIG. 8). Interestingly, in the HNP systems a weak signal with hyperfine coupling of aN=14.4G and aH=15.9G was also observed. This can be assigned to sulfite radical anions, which are typically generated by the reaction of hydrogen peroxide with sulfite (SO$_3^{2-}$) that may have been formed by photo-oxidation of the CdS rod surface.

FIG. 7D presents time-resolved EPR measurements, following the superoxide signal at static magnetic field of 3448G (star mark in FIG. 7C). A fast build-up of the signal was revealed during light illumination followed by a plateau when reaching equilibrium with the radicals consumed via further reactions. Decay of the signals was observed with the excitation light turned off. The plateau in the NRs case emerged at higher signal values than those of the HNPs, suggesting increased superoxide formation with the NRs. While this observation appeared contrary to the faster consumption of molecular oxygen by HNPs (FIG. 7A), this apparent discrepancy could be resolved considering that oxygen may be consumed also by the competing pathway forming directly H$_2$O$_2$ as seen in FIG. 5B for HNPs without SOD. Furthermore, superoxide can also react with hydroxyl radicals, which and as seen in FIG. 7B are indeed formed more efficiently by the HNPs compared to the NRs (FIG. 7B). Taken together, the various ROS detection assays, the polarography study, and the EPR infer the following complex scheme of radicals formation, as presented schematically in FIG. 9.

Light excitation of the semiconductor rods resulted in charge separation with the holes remaining on the rods and the electrons transferring to the metal tips. The electrons can reduce molecular oxygen to directly produce $H_2O_2$ or to produce superoxide that could be transformed to $H_2O_2$ by SOD. The holes on the other hand can oxidize water and hydroxide to produce hydroxyl radicals. Addition of hole acceptors effectively competes with direct formation of hydroxyl radicals by scavenging the holes. The acceptors may also neutralize hydroxyl radicals by secondary reaction. Notably, they have a major effect in diminishing the competing hole-electron back-recombination and hence significantly increase the reduction pathways leading either to direct or SOD catalyzed $H_2O_2$ formation.

After gaining these insights into the mechanisms of ROS formation by HNPs, an additional parameter affecting their photocatalytic activity was addressed: their surface coating. Surface coating effects on ROS formation by semiconductor nanocrystals were reported and for HNPs were studied in the context of the photocatalytic activity in hydrogen generation. To this end, nanoparticles were transferred to water by additional phase transfer techniques, including ligand exchange with glutathione (GSH) and 3-mercaptopropionic acid (MPA), or by poly(styrene-co-maleic anhydride) (PSMA), which is an amphiphilic polymer that coats the original hydrophobic ligands. HNPs with all these surface coatings have shown ROS formation and HRP activation. Interestingly, the surface coating was found to exert significant effects over HRP activation (FIG. 10A). The lowest production was observed for HNPs coated with PSMA. In comparison, HNPs coated with PEI showed the highest production efficiency with 5-fold higher product formation than thiolate ligands, such as GSH and MPA. Similarly, the rate and overall decrease in oxygen concentration was significantly lower for nanoparticles coated with GSH (FIG. 11A). Still, the GSH-coated systems showed similar trends of increased functionality of HNPs versus NRs regarding oxygen consumption, HRP activation, and hydroxyl radical formation (FIGS. 11B,C). The surface coating effect was reminiscent of but distinct from its effects on the photocatalytic activity for hydrogen production.

Whereas PSMA coating was reported to allow higher hydrogen production in comparison to thiolate ligands, this coating was found to be less favourable for production of hydrogen peroxide. This should be further investigated and may be attributed to different factors, such as the surface coating effect on HNPs surface defects passivation, band alignment, the ability of molecules to penetrate and migrate from the HNPs surface and the interaction of the surface coating with the formed radicals and peroxides.

The use of this concept in biological systems, where many biomolecules can interact and consume the produced radicals and hydrogen peroxide, was further investigated. To mimic the mammalian circulation conditions, the same set of experiments was reproduced in solutions containing 10% fetal calf serum (FIG. 12A). In the absence of hole acceptor, this set of experiments showed similar results for stimulating HNPs with or without serum. Interestingly, in the presence of ethanol as hole acceptor the kinetics of HRP activation using HNPs stimulation in solution was similar to or without serum in the first minutes. However, at longer irradiation times the HNPs in serum showed an improved stabilized behaviour over the HNPs in buffer, which showed slight kinetic decreases. This result may indicate the formation of a protein corona on the HNPs in serum that protects them. Nevertheless, as ethanol is not biologically relevant, various biological molecules were examined and confirmed for their ability to increase the photocatalytic capacity of HNPs under biological conditions (FIG. 13). This set of experiments supports the consideration of the quantification of ROS production, as was described above, to be valid for in vitro experiments and further predicts prospective use of HNPs stimulation for $H_2O_2$ production in biological systems.

Interestingly, measuring the activity of the cholinesterase enzymes in serum before and after the light illumination resulted in significant inhibition of their activity (FIG. 12C). Similar experiments with recombinant acetylcholinesterase (AChE) and butyrylcholinesterase (BChE) showed similar results. This may result from oxidation of amino acid residues in the active site gorge, similar to results observed following incubation of AChE with $H_2O_2$. Control experiments done in the absence of HNPs or in the presence of excess of catalase, an enzyme that hydrolyzes $H_2O_2$, minimized the inhibition effect; confirming the suggested mechanism of inhibition via light-induced production of $H_2O_2$ by the HNPs.

This provides another example for the ability to effect the function of biomolecules with HNPs by light-induced ROS production. Furthermore, impairment of cholinesterase enzymes activity was found to be involved in numerous pathologies, including myasthenia gravis, type-2 diabetes mellitus and Alzheimer's and Parkinson's diseases, cardiovascular disease, inflammation, stress, stroke, anxiety, Sjögren's syndrome, etc. This has led to a yet unfilled demand to affect the activity of the cholinesterase enzymes in high spatial-temporal manner for both basic research and therapeutics. Alzheimer's disease, Myasthenia gravis and Sjögren's syndrome are only few examples of pathologies which were suggested and/or treated today with anti-cholinesterases. For example, eye drops containing cholinesterase inhibitors, such as hydroxychloroquine were suggested as treatment for Sjögren's syndrome [Dawson et al., Rheumatology (Oxford). 2005 44(4):449-55]. Replacing recurring treatment with organic molecules by photo-chemically stable HNPs that following a single treatment can continuously inhibit the cholinesterase activity in a controlled manner is one non-limited example that can benefit from this technology disclosed herein.

To further address this potential, the biotoxicity of HNPs was investigated for the first time. For this purpose, the biocompatibility of the HNPs was examined by incubating cultured K-562 human bone marrow cells for 24 h under dark conditions with different concentrations of HNPs or NRs coated with GSH. In these sets of experiments, GSH surface coating was used to minimize toxicity resulting from the use of PEI. FIG. 10B shows the results of an MTT viability assay, presenting no significant effects for either NP types following incubation with low NP concentrations, and limited toxicity when exposing the cells to similar concentrations of HNPs as those used for HRP stimulation (highest concentrations). These results were also supported by "live and dead" bioassay, which is based on staining mitochondrial ATPase that decorates live cells in fluorescent green and dead cells in red. Under dark conditions, HNPs did not show significant toxicity with the highest tested concentration (FIG. 12B).

The effect of ROS formation following light excitation on cell viability was also examined. FIG. 10C shows results of "live and dead" assay after short illumination with 405 nm 20 mW/cm LED on the K-562 cells following their incubation for 1 h with 2.5 nM (left) and 0.5 nM (right) of HNPs. For the higher HNPs concentration, the enhanced oxygen consumption and ROS production, as measured in the presence of fetal calf serum, lead to significant cells' death (FIG. 10C left). This observation suggests the possible utilization of these HNPs in photodynamic therapy applications. On the other hand, lower HNPs concentration mainly manifested live cells, consistent with limited ROS formation (FIG. 10C right). This finding demonstrated that light-controlled production of ROS by HNPs can be performed without significant cell damage, and hence leaves open the doorway to utilize them for light-mediated modulation of biological activity. Notably, in these experiments with GSH coating some cellular uptake is expected that can be minimized by different surface coatings as shown for semiconductor nanocrystals over-coated with PEG.

In conclusion, ROS formation was demonstrated herein via light irradiation of HNPs, showing significantly improved yield over NRs, and studied the various oxidation/reduction processes taking place in physiologically relevant conditions. Both systems produce superoxide radicals, while HNPs also showed an enhanced capacity to produce hydrogen peroxide and hydroxyl radicals in comparison to bare nanorods. The demonstrated ability to activate HRP by light using HNPs as a proof of concept for a general approach of applying such systems for modulating enzyme properties and affecting biological pathways through radicals and/or peroxides formation.

Moreover, the ability to control nanoparticle properties by tuning the energy band alignment can open further new avenues for efficient modulation of specific biological pathways involving redox reactions with visible light. The addition of hole acceptors and SOD increases the efficiency of $H_2O_2$ production and can serve for increasing the specificity of the system by minimizing the diffusion and undesired interaction of radicals from the HNPs surface to biomolecules other than the peroxidases. Biotoxicity studies demonstrate the versatile utilization of HNPs in biomedical application by tuning the extent of ROS production. Aggressive production may be used for photodynamic therapy; in comparison, cell viability was reasonably maintained under the light-controlled limited formation of ROS.

HRP is widely used in detection and quantification methods and other peroxidases play roles in metabolic and immune pathways, highlighting the relevance of this approach to biological processes. In fact, some peroxidases are expressed and function mainly outside the cells, which further limits toxicity concerns due to internalization of HNPs and intracellular ROS production. For example, thyroid peroxidase plays its biological role by incorporating hydrogen peroxide to thyroid hormones on the apical membrane of the thyroid follicular cell.

Additionally, HNPs can be conjugated to delivery agents and to substrates, including implantable substrates, to provide local specific ROS production on-demand, paving the way for their use in unique biomedical applications.

The invention further provides use of a plurality of HNPs in a method of polymerization.

Polymerization of photo-curable (or photo-polymerizable) systems has been extensively used in advanced coatings (wood/automotive), adhesives and printing inks for 2D and 3D printing (of any material, pattern or object). In this process a photo-initiator is a compound which absorbs light and generates reactive species. It plays a crucial role in determining the rate of photo-initiation, the most critical step in a photo-polymerization process, which determines the kinetics and properties of the resulting polymerized objects. Photo-initiation is directly proportional to the incident light intensity, the concentration of photo-initiator and the intrinsic properties of the photo-initiator. The intrinsic properties of the photo-initiator that influence its utility are the optical density (O.D), the quantum yield or cleavage events that occur per photon absorbed, and the photo-initiator efficiency or the ratio of initiation events to radicals generated by photolysis. For efficient polymerization, the initiator should have a large optical density and good overlapping absorbance spectrum with the emission spectrum of the light sources.

Currently available photo-initiators undergo chemical cleavage upon irradiation and generate short-lived radicals; which are consumed during the process. Thus, to perform an elongated photo-polymerization, high concentration of photo-initiator is often required. Furthermore, they exhibit low efficiency and slow rate of polymerization upon irradiation with light sources having wavelengths in near UV-visible region (300-700 nm). Additionally, poor water-solubility of these photo-initiators limits their use in aqueous systems with photo-curable monomers. Hence, the HNPs disclosed herein fulfil the unmet need for highly efficient photo-initiators, with high absorbance in near UV-visible range, which can be used for high-performance photo-polymerization and that can be used at various wavelengths by proper tailoring its structure. Thus, the HNPs provide the opportunity for developing an efficient catalytic multi-functional photo-initiator system that offers several functional and economical productivity advantages.

It is widely known that free-radical photo-polymerization is affected negatively by oxygen inhibition. Oxygen inhibition is a process wherein oxygen quenches the initiating and/or growing of polymer radicals. As disclosed herein HNPs consume oxygen and generate reactive oxygen species, which participate in the polymerization process. Thus, the "dual-nature" of HNPs, consuming oxygen and generating polymerization initiating radicals, contribute to the high polymerization efficiency in aqueous polymerizing inks.

The HNPs are further used herein as photo-initiators in polymerization reactions in a variety of applications. In some embodiments, the HNPs are utilized as photo-initiators in printing processes, in combination with ink components.

In some embodiments, the HNPs are utilized as photo-initiators for high-performance polymerization in rapid 2D or 3D printing, which requires generating free radicals efficiently, following irradiation in the visible or near UV-visible region, to induce polymerization processes.

Thus, by an additional aspect of the invention, there is provided a printing formulation, e.g., ink, comprising a photo-initiator according to the invention.

The printing formulation may be in the form of a photo-curable ink comprising a plurality of HNPs and at least one polymerizable material in the form of at least one monomer, at least one oligomer, at least one pre-polymer or any combination thereof. In some embodiments, the plurality of HNPs is present in a catalytic amount.

In some embodiments, the ink composition optionally further comprises at least one additive selected from solvents, dispersants, reactive diluents, humectants, surfactants, rheological agents, ionic materials, organic solvents, dyes, pigments, stabilizers, accelerators, inhibitors, enzymes, electron and/or hole acceptor and wetting agents.

The photocurable ink may be formulated in any solvent or liquid media, selected from organic solvents and water-based solvents or mixtures, making them suitable for a variety of applications e.g., for biomedical application such as 2D and 3D printing with biomolecules, nutrients or live cells, and within any water-based polymerizable inks. Such control is uniquely available for the photo-initiators of the invention, where their solvent compatibility can be modified by suitable surface chemistry modifications.

The present invention further concerns aqueous dispersions of said HNPs for use in a method of preparing photocurable inks, wherein the method optionally comprises mixing the aqueous dispersion with a material to be polymerized.

The present invention further concerns a powder for dispersion in water, said powder comprising HNPs. The powder or water may optionally further comprise at least one additional additive conjugated or free such as at least one dispersant, electron and/or hole acceptor, enzyme and more. A non-limiting example being polymers (e.g. polyethylene glycol (PEG), polyethyleneimine (PEI), poly styrene-co-maleic anhydride (PSMA)), peptides (e.g. glutathione), DNA and RNA molecules, thiolate ligands (e.g. mercaptoundecanoic acid (MUA), mercaptohexanoic acid (MHA), mercaptopropionic acid (MPA), mercaptosulfonic acid (MSA), dihydrolipoic acid (DHLA)), alcohols (e.g. ethanol and methanol), sulfides, triethanolamine, acids (e.g. pyruvate, ascorbate, lactate, succinate, EDTA), amino acids, carbohydrate (e.g. glucose, sucrose), ubiquinol, NADH, NADPH, FAD, cations and/or anions and/or their salts, redox dyes, C60, superoxide dismutase and cytochromes.

In a powder form, the HNPs may be present as solid nanoparticles or may be combined with at least one solid carrier such as a polymer or a matrix material or another solid material in order to stabilize, protect or reduce the nanoparticles density in a powder volume. In some embodiments, the HNPs are used in a particulate form. For example, a powder is prepared such that upon dispersion in water, a concentration of $6 \times 10^{-7}$ M of nanoparticles, with particle sizes less than 100 nm is obtained.

The term "photo-initiator" refers to HNPs capable of initiating polymerization processes by forming free radicals upon light exposure. Such processes may be any printing technology involving light activated polymerization reactions, such as two-photon absorption (TPA) printing processes, and other light initiated 2D, or 3D and other printing processes.

The polymerizable materials, such as monomers, oligomers and pre-polymers, utilized in any polymerization reaction, e.g., in 2D or 3D UV cured printing processes, may be selected from any such materials that can undergo a polymerization reaction. In some embodiments, the polymerizable materials may be selected from acid containing monomers, acrylic monomers, amine containing monomers, crosslinking acrylic monomers, modified gelatin acrylates, modified water-soluble/water-dispersible urethane oligomers and monomers, modified water-soluble/water-dispersible acrylates, dual reactive acrylic monomers, epoxides/anhydrides/imides, fluorescent acrylic monomers, fluorinated acrylic monomers, high or low refractive index monomers, hydroxy containing monomers, mono and difunctional glycol oligomeric monomers, styrenic monomers, acrylamide monomers, vinyl and ethenyl monomers, and corresponding oligomers and pre-polymers.

The present invention further concerns a method for providing dispersion of HNPs, e.g., for use in the preparation of inks for 1D or 2D or 3D printing, the method comprising dispersing in a liquid medium a plurality of said HNPs, said medium comprising one or more of the ink components as recited herein. In some embodiments, the dispersion is an aqueous dispersion comprising the HNPs.

The present invention further provides a printing process, the process comprising patterning an ink formulation on a substrate surface, the ink formulation, and the pattern formed, comprising a plurality of HNPs and at least one polymerizable material, and irradiating said pattern comprising said HNPs to cause polymerization of said polymerizable material present in the pattern.

The present invention further provides a printing process, the process comprising forming a pattern on a substrate surface, the pattern comprising a plurality of HNPs and at least one polymerizable material, and irradiating said pattern comprising said HNPs to cause polymerization of said polymerizable material present in the pattern.

The method may be utilized for fabricating 2D patterns by any printing technology that makes use of polymerization, e.g., photo-polymerization, such as stereolithography by digital processing printing, and inkjet printing followed by polymerization.

The pattern may be a pattern of any shape or structure. The features of the pattern (e.g., lines) may be of any size, thickness and length. For example, the pattern may be in the micrometer or in the nanometer regime. In other cases, the pattern may be a visible pattern. The pattern may be formed by any one printing method known in the art or by any combination of such methods.

The present invention further contemplates a method of fabrication a 3D object, the method comprising deposition of a material, e.g., layer-by-layer, on a surface or on a previously formed (layered or deposited) layer, the material being in the form of a formulation or a composition comprising a plurality of HNPs and at least one polymerizable material, and irradiating said pattern to cause polymerization of said material. Irradiation may be after each layer has been deposited, after several layers have been deposited or after the full object has been formed.

The method permits construction of a variety of objects, not only by direct printing or by bottom-up methods. In some embodiments, the deposition is by printing, e.g., ink jet printing. In other embodiments, the deposition is by any other deposition technique known in the art.

As used herein, "printing" of a pattern may be achievable by any printing technology known in the art, including, e.g., differential roll printing, contact printing, inkjet printing, laser printing, screen printing, flexographic printing, digital light processing printing, coating, spray coating, spin coating, ink placing, deposition or any combination thereof, provided that any one component of the ink formulation comprises HNPs according to the invention. In some embodiments, the printing is differential roll printing, contact printing or inkjet printing. In some embodiments, said printing is inkjet printing.

In some embodiments, for 2D printing the printing technology is inkjet printing, laser printing, screen printing or flexographic printing.

In some embodiments, for 3D printing the printing technology is inkjet printing or digital light processing printing.

The object thus formed may be of any size and shape and may be tailored, inter alia, based on the photo-initiator utilized. In some embodiments, the object is in the form of a matrix such as a photocurable water-based matrix, e.g., a hydrogel, suited for any application, such as scaffolds for medical implants, and biotechnological processes. For certain applications, the ink formulation may further comprise one or more functional materials intended to provide functionality to the printed polymeric structure. Among them, without limitations, are conductive materials or precursors for conductive materials (such as metallic nanoparticles and metal precursors, carbon nanotubes, graphene and their derivatives, conductive polymers), biological materials (such as cells and microorganisms, proteins and peptides, polysaccharides), special effect colorants (such as fluorescent, responsive materials) and sensing materials.

As the HNPs are not consumed by the photo-polymerization reaction and may be initiated for further use by light irradiation, the HNPs present in a printed or otherwise formed object according to methods of the invention, may be activated after the object has been constructed to impose a variety of structural, mechanical, physical or chemical changes in the object. For example, the HNPs may be in the form of a blend comprising multiple (two or more) different populations of HNPs, activatable by irradiation by different wavelengths, such that irradiation by one wavelength would cause polymerization of a single region of the object, while subsequent irradiation under light of a different wavelength would cause polymerization of another region of the object. This enables step-wise or on-demand polymerization.

Thus, the invention further provides a cured or partially cured pattern or object comprising a plurality of HNPs distributed in the pattern or object material. In some embodiments, the pattern or object has been previously photocured, the photo-initiator being the HNPs. In other embodiments, the pattern or object has been previously photocured, the photo-initiator not being the HNPs. In some embodiments, the pattern or object has been previously cured with an initiator being different from a photo-initiator.

Therefore, the invention further contemplates a photocurable pattern or object comprising a plurality of HNPs.

Dental composites comprising photocurable materials or resins may also be manipulated utilizing HNPs, as disclosed herein.

Thus, the invention further contemplates a dental composition, comprising a plurality of HNPs, as defined herein, at least one polymerizable resin, e.g., monomer, oligomer, pre-polymer, etc; and at least one filler, optionally an inorganic filler. Once the composition is positioned and shaped, it is irradiated to thereby activate the HNPs to cause polymerization of the at least one polymerizable resin.

The composite may be used in vivo or ex vivo in the structuring of at least one dental article, such as crowns, bridges, denture teeth, inlays, on-lays, implant abutments, veneers, implants, implant accessories, implant posts, a filler or a dental mill blank.

As the HNPs provide the opportunity for sequential or on-demand photo-polymerization, the dental composite may be prepared ex vivo into a composite of certain toughness, by first exposing the composite to light of a first wavelength, and after its positioning in vivo expose the composite to light of a further wavelength to endow the composite with the required mechanical and physical properties.

The invention thus provides a photo-initiator for use in a method of photo-polymerization, the photo-initiator consisting hybrid nanoparticles (HNPs), e.g., for polymerization of a photo-curable material. In some embodiments, the method of photo-polymerization is printing. In some embodiments, the HNPs are selected to form a reactive species upon irradiation by light in the visible regime, near IR regime or UV regime, the reactive species being a radical or a reactive oxygen species.

Thus, further provided is a printing formulation comprising a photo-initiator in the form of HNPs. The formulation may further comprise at least one polymerizable material, selected from at least one monomer, at least one oligomer, at least one pre-polymer and any combination thereof.

The formulation may further comprise at least one additive selected from a solvent, a dispersant, a reactive diluent, a humectant, a surfactant, a rheological agent, an ionic material, an organic solvent, a dye, a pigment, a stabilizer, an accelerator, an inhibitor, an enzyme, an electron and/or hole acceptor and a wetting agent.

The formulation may comprise at least one solvent selected from organic solvents and water-based solvents.

Alternatively, the formulation may be in powder form, e.g., in a form ready for dissolution, suspension or dispersion in a liquid carrier, wherein said liquid carrier is selected from organic solvents and aqueous-based solvents. Such solid formulations may further comprise a variety of additives selected from at least one dispersant, at least one electron acceptor material and at least one hole acceptor material.

Formulations of the invention may further comprise at least one material selected from peptides, nucleotide molecules, thiolate ligands, mercaptoundecanoic acid (MUA), mercaptohexanoic acid (MHA), mercaptopropionic acid (MPA), mercaptosulfonic acid (MSA), dihydrolipoic acid (DHLA), alcohols, sulfides, triethanolamine, organic acids, amino acids, carbohydrates, ubiquinol, NADH, NADPH, FAD, cationic materials, anionic materials, organic salts, inorganic salts, redox dyes, $C_{60}$, superoxide dismutase and cytochromes.

The at least one polymerizable material is typically selected from acid containing monomers, acrylic monomers, amine containing monomers, crosslinking acrylic monomers, modified gelatin acrylates, modified water-soluble/water-dispersible urethane oligomers and monomers, modified water-soluble/water-dispersible acrylates, dual reactive acrylic monomers, epoxides/anhydrides/imides, fluorescent acrylic monomers, fluorinated acrylic monomers, high or low refractive index monomers, hydroxy containing monomers, mono and difunctional glycol oligomeric monomers, styrenic monomers, acrylamide monomers, vinyl and ethenyl monomers, and corresponding oligomers and pre-polymers.

The invention also provides a printing process comprising patterning an ink formulation on a surface region, the ink formulation comprising a plurality of HNPs and at least one polymerizable material, and irradiating said pattern to cause polymerization of said polymerizable material.

Also provides is a printing process comprising forming a pattern on a surface region, said pattern comprising a plurality of HNPs and at least one polymerizable material, and irradiating said pattern to cause polymerization of said polymerizable material.

As explained herein, irradiation induces formation of at least one reactive species selected from a radical and a reactive oxygen species, which causes polymerization of the polymerizable material.

When processes of the invention are carried out for printing 1D, 2D or 3D objects, patterning of object constructing may be achievable by printing, e.g., inkjet. Where 3D objects are concerned, the printing or patterning may involve patterning an ink formulation on a surface region or on a pattern having been formed on said surface region, and optionally repeating the patterning one or more additional times, to obtain a multi-layered object comprising two or more layers, and irradiating to cause polymerization of a polymerizable material in said ink formulation. Irradiation may be carried out after, during, or concomitant with the patterning steps or after several layers have been deposited or after the full object has been formed. Such a process may be utilized in the construction of self-standing objects, which are detachable from the original surface on which they were constructed. Such objects comprise a plurality of HNPs which may be further utilized for inducing additional modifications in the object.

For achieving on-demand activation of the HNPs, in some embodiments it is preferable to utilize at least two populations of nanoparticles, each population being reactive under light of a different wavelength. For example, one of said at least two populations may be activatable by light of a first wavelength for forming said pattern or object, and at least one other population of said at least two populations may be unreactive when irradiated under said light of a first wavelength.

Object formed according to processes of the invention are highly desirable as they comprise a population of HNPs which has not been consumes in the production of the object. The object may be of any size, shape, material and constitution. In some embodiments, the object is a material matrix, or a hydrogel, that is typically biocompatible, and thus may be utilized in medicine or in a variety of biological applications as disclosed herein.

The invention also provides a polymeric object comprising at least one polymerizable material and at least two populations of HNPs, each population being activatable under light of a different wavelength to cause polymerization of the at least one polymerizable material.

Also provided is a photo-reactive object comprising a plurality of HNPs and at least one polymerizable material, the HNPs being capable of causing polymerization of the at least one polymerizable material upon light irradiation.

A dental composite which comprises at least one photo-curable material and a plurality of HNPs, is also provided, comprising a plurality of HNPs, at least one polymerizable resin in a form selected from monomers, oligomers and pre-polymers, and optionally at least one filler.

The HNPs may be used in a variety of different applications and are therefore made into commercial packages or kits which comprise in addition to a plurality of the HNPs, a medium for carrying out a diagnostic analysis for determining the presence or absence of at least one material; or for carrying out a synthetic transformation of at least one material, depending on the utility of the kit, and instructions for carrying out said analysis and/or synthetic transformation under exposure to light.

A method is also provided for generating a reactive species in the form of a radical or a peroxide in a medium, the process comprising irradiating a medium comprising HNPs and at least one material susceptible of radical or peroxide-mediated conversation.

Similarly provided is a method for generating a reactive species in the form of a radical or a peroxide in a biological medium, the process comprising irradiating said medium comprising HNPs and at least one biological material susceptible for radical or peroxide-mediated conversation, for controlling a biological process associated with said at least one biological material, through illumination. The at least one biological material may be an enzyme. The method may be used for affecting a biological pathway through radicals or peroxide formation.

As such, the invention also contemplates a biological medium comprising an enzyme and a plurality of HNPs.

The tool for generating reactive species, selected from peroxides and radicals, is in the form of a plurality of hybrid nanoparticles (HNPs), as defined herein. This tool may be used in a method of generating reactive oxygen species in solution, in photopolymerization reactions, may be used in printing, as a photo-initiator and for a variety of other purposes. The reactive species may be formed by irradiating a formulation, suspension or dispersion comprising the HNPs and at least one material capable of radical formation. In some embodiments, the material capable of radical formation is at least one material capable of accepting at least one unpaired charge from the HNPs, or which dissociates upon irradiation by light in the presence of the HNPs into a reactive species, wherein the at least one material is selected from an atom, a molecule, and an ion. The at least one material may be selected from water, hydroxide, oxygen, peroxides, an azo compound, a disulphide, a persulfate, carbon dioxide, carbonate, azide, ammonia, hydroxylamine, nitrogen dioxide, nitrogen trioxide, a phosphite, a phosphate, sulfur dioxide, a sulphite, a sulfate, peroxomonosulfate, selenite, dithiocyanate, a dihalogen, chlorine and bromine dioxide.

The invention also contemplates a photo-initiator in the form of a hybrid nanoparticle (HNP), or a formulation comprising at least one photo-initiator material consisting of a hybrid nanoparticle (HNP), or a formulation comprising a plurality of HNPs and at least one material capable of being catalytically transformed by a reactive species selected from a radical and a peroxide.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1A—Absorption spectra of CdSe/CdS NRs and CdSe/CdS—Au HNPs, showing similar features. The contribution of the small Au tips is mainly manifested in the small increase of the absorption tail toward the red. Inset-TEM image presenting matchstick-like structure of 52±4 nm×4.4±0.4 nm CdSe/CdS nanorods with small gold tips on their apex (stronger contrast, 1.6 nm in diameter). FIG. 1B—Staircase behavior of HRP stimulation while turning off and on the excitation source, indicated by black and grey arrows, respectively. (Inset) Detection of HRP product by absorbance measurements with its characteristic peak around 495 nm, growing with increased irradiation times of the HNP and HRP solution.

FIG. 4A—Reaction scheme for production of quinoneimine catalyzed by HRP in the presence of 4-AAP and phenol upon light stimulation of HNPs. FIG. 4B—Control measurements of photo-induced modulation of HRP activity by HNPs were done in various conditions, absence of enzyme or oxygen, without irradiation and absence of HNPs. The result of the full assay which includes all these parameters is shown in the black curve.

FIGS. 5A-C provide comparative study of product formation by HRP activation using HNPs, NRs, and QD seeds in different conditions. FIG. 5A—Light stimulation of hybrids in the presence of SOD and ethanol results in 3- and 15-fold higher product formation after 500 s, than when stimulating bare nanorods or CdSe seeds, respectively. FIGS. 5B-C—Comparative bar charts for the HRP activity in different conditions, plotting product formation after 500 s (note the different scale in FIGS. 5B-C). Addition of SOD to the solution increases the efficiency of all of the tested nanoparticle systems and the efficiency is further enhanced upon adding the hole acceptor (HS), which is ethanol in this case. Notably, the hole acceptor and SOD effects on the efficiency of the HNPs system was much more pronounced compared to the NRs and QDs.

FIG. 7A-Kinetic measurements of molecular oxygen consumption by HNPs and NRs coated with PEI upon light illumination using polarography. FIG. 7B—Kinetic measurements of hydroxyl radical formation using the fluorescence TPA assay (inset). Note the significantly faster and more efficient hydroxyl radicals production upon stimulation of HNPs in comparison to NRs. Addition of ethanol as a hole scavenger to the hybrids solution prevented this reaction, yielding similar signals to those of control TPA alone. FIG. 7C—EPR measurements following excitation of HNPs (upper panel) and NRs (lower panel), and corresponding fits. The results show near-solely (90%) superoxide production for the bare NRs, whereas the HNPs signal reveals additional peaks which are attributed to significant hydroxyl radicals production. FIG. 7D—Time-resolved measurements for the superoxide radical signal at static magnetic field of 3448G (star mark in panel c) show higher superoxide signal buildup for NRs over HNPs, followed by a plateau when light is on (grey arrows), resulting from balanced formation and destruction of the radicals. Fast decay of the radical signal is seen upon turning off the excitation source (black arrows).

FIG. 10A-HRP activity upon light stimulation of HNPs with different surface coatings in the presence of SOD and ethanol. HNPs coated with PEI show 5-fold higher efficiency in comparison to thiolate ligands, such as GSH and MPA. PSMA showed the lowest efficiency. FIG. 10B—MTT viability assay with cultured K-562 cells shows that their incubation for 24 h with different concentrations of NRs and HNPs did not significantly affect their viability. FIG. 10C—Live and dead assay 24 h after illumination on cells incubated with 2.5 and 0.5 nM of HNPs (left and right, respectively). Higher HNPs concentration shows significant cells' death (non-bright cells in the figure), an outcome that indicates a potential use for photodynamic therapy. Lower HNPs concentration showed mostly live cells (bright cells), suggesting cells' viability under light-controlled ROS production, scale bar is 100 µm.

FIG. 11A—Kinetic measurements of molecular oxygen consumption by HNPs and NRs coated with GSH upon light illumination, measured by polarography. FIG. 11B—Comparison of HRP activity upon light irradiation using the HRP activity assay between CdSe/CdS—Au HNPs and CdSe/CdS NRs coated by GSH in the presence of SOD and hole scavenger (e.g. EtOH) and in the absence of these additives. FIG. 11C—Kinetic measurements of hydroxyl radical formation using the TPA assay showing faster hydroxyl radical production upon stimulation of hybrids in comparison to bare nanorods. Addition of ethanol as a hole scavenger to the hybrids solution prevents this reaction, yielding similar signals to those of control TPA alone.

FIG. 12A—The production of HRP's product after stimulating HNPs in serum or in buffer with or without addition of hole acceptor to the solution. The results demonstrate the ability to use HNPs stimulation with and without hole acceptor for efficient and controlled production of hydrogen peroxide also in biological systems. FIG. 12B—Live/Dead assay confirms incubation of K-562 cells with HNPs for 24 hr under dark conditions didn't affect their viability (most cells are stained in green, bright in the figure), Scale bar is 100 µm. FIG. 12C—The activity of the cholinesterase enzymes is inhibited following light-induced production of ROS by HNPs but not by the irradiation itself.

FIGS. 14A-C show polymerization kinetics: percent conversion of vinyl bonds calculated using aqueous acrylamide solutions with nano-photoinitiator catalysts (hybrid CdS—Au Nanorods stabilized with PEI, 6E-7 M) at 988 cm$^{-1}$ (assigned to out-of-plane bending mode of the =C—H unit) normalized to the C=O stretching peak at 1654 cm$^{-1}$ as an internal standard, at varying UV (385 nm) exposure duration. FIG. 14A—CdS—Au show higher polymerization efficiency than bare CdS. FIG. 14B and FIG. 14C present light-induced polymerization using diverse CdS—Au HNPs concentration and excitation wavelengths.

FIGS. 15A-B show a 3D printed hydrogel with an buckyball architecture, prepared using nano-photoinitiator catalysts (Hybrid CdS—Au Nanorods stabilized with PEI) according to the invention. The 3D printed hydrogel was prepared with CdSe/CdS NRs in the formula resulting in fluorescence architecture, providing an example of a 3D printed material that becomes functional by a second excitation wavelength.

FIG. 17A presents an image of ZnSe—Au HNPs as an example for Cd free system that can be used for applications requiring the light-induce ROS formation. FIGS. 17B-C present images of a mixture of acrylamide monomers with ZnSe—Au NPs, before and after UV exposure. Upon the radiation, the liquid drop polymerized forming gel structure.

DETAILED DESCRIPTION OF EMBODIMENTS

Figure 1A:
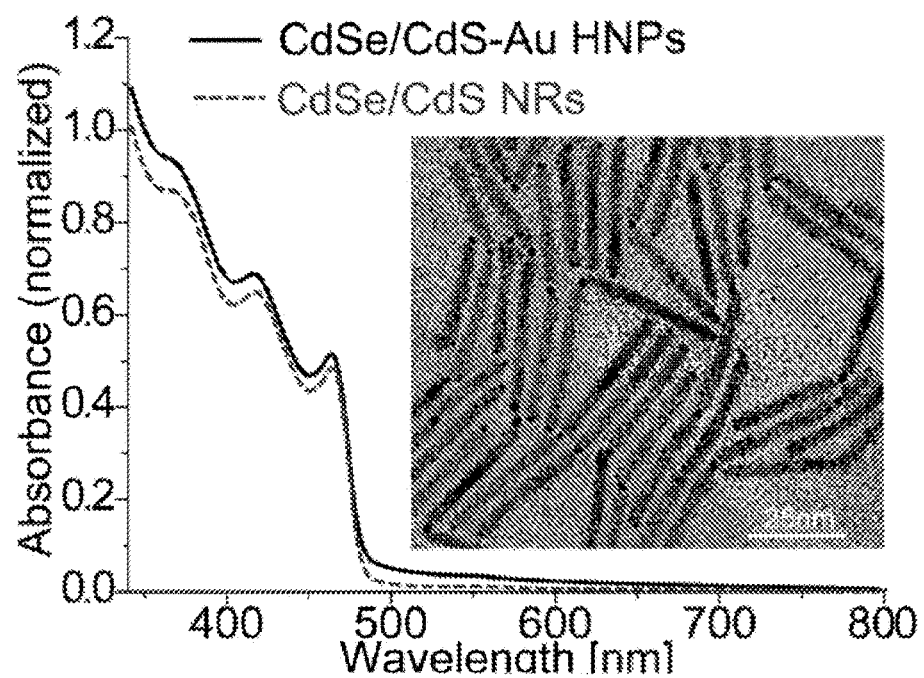
FIGS. 1A-B show optical and structural characterization of HNPs along with their HRP photocatalytic activation.
Figure 1B:
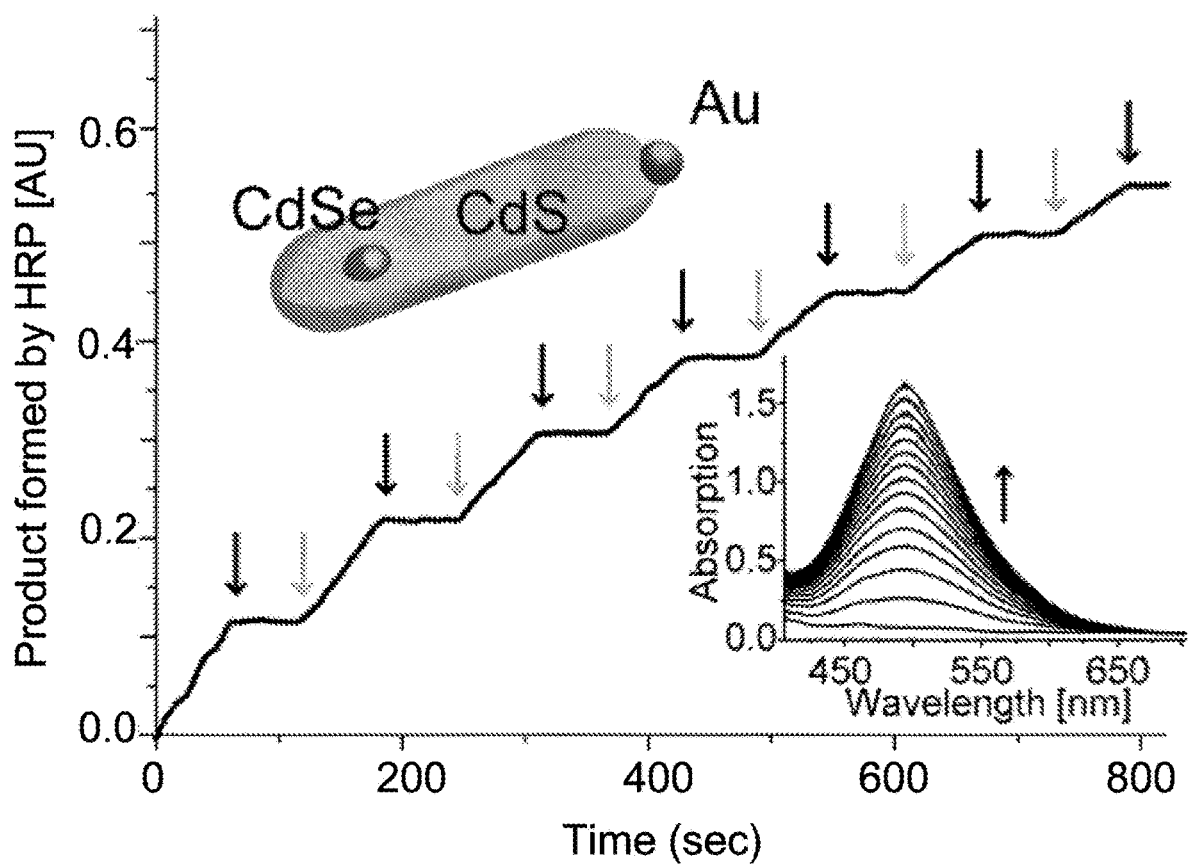
Figure 2A:
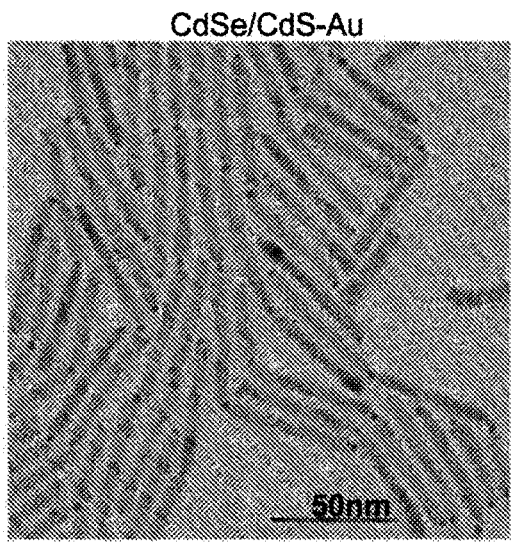
FIGS. 2A-H show TEM images of hybrid nanorods CdSe/CdS—Au (52 nm×4.4 nm) (FIG. 2A) and CdS—Au (49 nm×4.2 nm) (FIG. 2E). Sizing histograms for rods diameter (FIGS. 2B,F), length (FIGS. 2C,G) and Au metal domain diameter (FIGS. 2D,H).
Figure 2E:
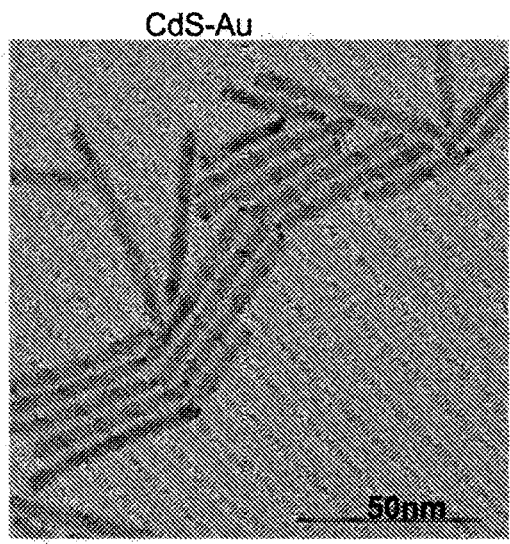
Figure 2B:
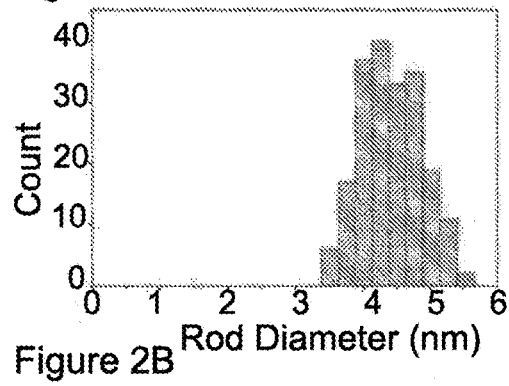
Figure 2F:
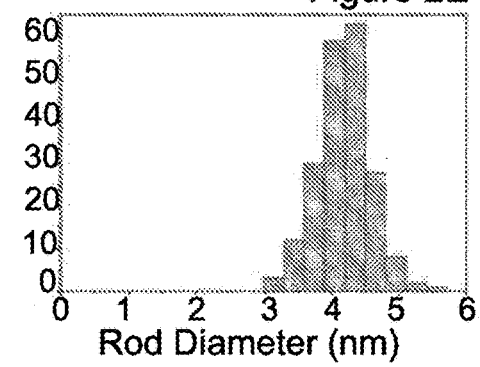
Figure 2C:
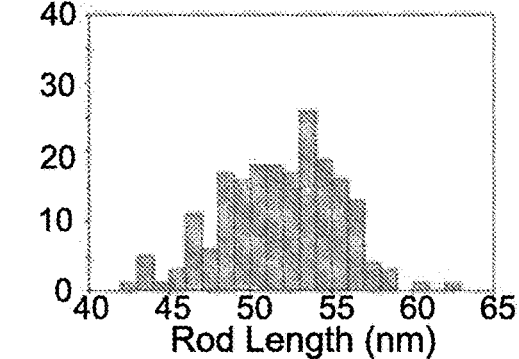
Figure 2G:
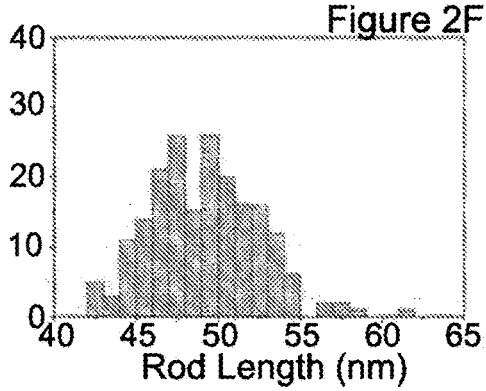
Figure 2D:
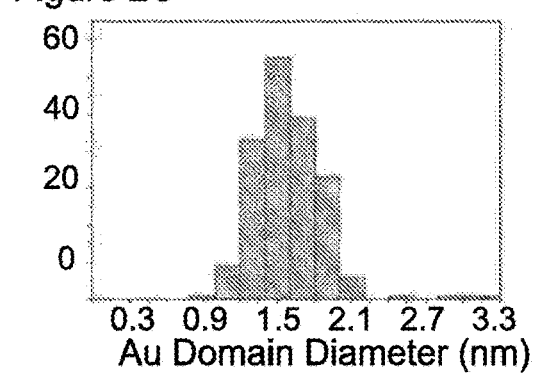
Figure 2H:
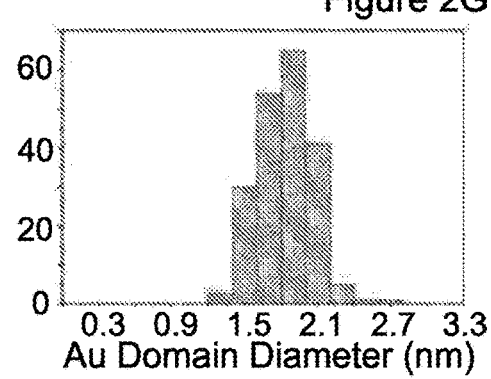

The invention discloses high-performance photo-initiators in the form of hybrid nanoparticles (HNPs) which may be used in a variety of applications, ranging from biological and chemical applications to industrial applications.

The HNPs are light-activated hybrid nanoparticles comprising each at least one metal/metal alloy region and at least one semiconductor region having an absorption onset in the UV (200-400 nm), or the visible (400-700 nm) or the near infrared (NIR) range (0.7-3 µm). In some embodiments, the at least one semiconductor region has an absorption onset in the range of 350 nm to 3 µm. In some other embodiments, the at least one semiconductor region has an absorption onset in the range of 450 nm to 3 µm. In further embodiments, the at least one semiconductor region has an absorption onset in the range of 470 nm to 3 µm. In still other embodiments, the at least one semiconductor region has an absorption onset in the range of 500 nm to 3 µm.

In some embodiments, the HNPs comprise at least one metal/metal alloy region and at least one semiconductor region having an absorption onset in the UV (200-400 nm, in some embodiments above 350 nm, in some embodiments above 380 nm), or the visible (400-700 nm, in some embodiments above 420, or above 450 or above 500 nm) to near infrared (NIR) range (0.7-3 µm), said nanoparticle being capable of forming, upon irradiation (illumination) with a radiation in the visible and/or NIR range, an electron-hole pair at the metal/semiconductor interface and subsequently undergo charge separation. In certain embodiments, where the nanoparticles have elongated shape, they may be prepared as disclosed in WO 05/075339, or a US application derived therefrom, herein incorporated by reference. However, the shape and size of the nanoparticle so defined may vary and is not restricted to the elongated structure.

In some embodiments, the HNPs comprise at least two metal/metal alloy regions, separated by at least one semiconductor region, wherein each of said at least two metal/metal alloy regions is of a different or same metal/metal alloy material. In some embodiments, each of said at least two metal/metal alloy regions is of a different metal/metal alloy material (having different Fermi potentials). In some embodiments, the two metal/metal alloys are of the same metal/metal alloy material.

In other embodiments, the HNPs comprise at least two metal/metal alloy regions, separated by at least two semiconductor regions, wherein each of said at least two metal/metal alloy regions is of a different or same metal/metal alloy material, and each of said at least two semiconductor regions having a different energy gap and/or different energy band positions.

In some embodiments, the at least two semiconductor regions are separated by at least one metal/metal alloy region. In other embodiments, said at least two semiconductor regions are not separated by one or more metal/metal alloy region and are therefore referred to herein as "sub-regions". The two or more semiconductor sub-regions are each of a different semiconductor material.

Within the context of the present invention, the term "material" refers to a solid substance of which the nanoparticles or any one region thereof is made. The material may be composed of a single substance, e.g., elements, alloys, oxidized forms, etc, or a mixture of such substances, at any ratio.

The HNPs employed by the methods of the invention, are discrete entities wherein at least one of its dimensions (e.g., diameter, length, etc) is between 1-20 nm. They may have rod-like structures having lengths of below 400 nm, preferably below 200 nm.

Notwithstanding the above, the HNPs can have any shape and symmetry, and may display branched and net structures. Without being limited thereto, the HNPs may be symmetrical or unsymmetrical, may be elongated having rod-like shape, round (spherical), elliptical, pyramidal, disk-like, frame structure, branch, network or have any irregular shape.

In some embodiments, the HNPs are nanorods having elongated rod-like shape. In some other embodiments, the nanorods are constructed of a semiconducting material having at one or both ends a metal or metal alloy region.

The plurality of HNPs refers to a population of nanoparticles optionally having a narrow size distribution, shape distribution and/or a spatial arrangement, namely the arrangement of the metal/metal alloy region in relation to the semiconductor region and/or the spatial distribution of the metal/metal alloy regions on the surface of the semiconductor material. In some embodiments, the population of HNPs is not homogenous but rather tailored to sequential processes, e.g., a step-by-step process wherein each step utilizes a different population of HNPs.

The HNPs comprise a semiconducting material selected from elements of Group II-VI, such as CdSe, CdS, CdTe, ZnSe, ZnS, ZnTe, HgS, HgSe, HgTe and alloys thereof such as CdZnSe; Group III-V, such as InAs, InP, GaAs, GaP, InN, GaN, InSb, GaSb, AlP, AlAs, AlSb and alloys such as InAsP, CdSeTe, ZnCdSe, InGaAs; Group IV-VI, such as PbSe, PbTe and PbS and alloys thereof; Group such as InSe, InTe, InS, GaSe and alloys such as InGaSe, InSeS; Copper chalcogenides such as CuS, $Cu_2S$ and other stoichiometry as in $Cu_{2-x}S$ with x ranging from 0 to 1; semiconductors such as $CuInS_2$ and $CuInxGa_{1-x}Se_2$; Oxides such as ZnO, $TiO_2$, $In_2O_3$, CuO, $Cu_2O$, and others; Group IV semiconductors, such as Si and Ge alloys thereof, and combinations thereof in composite structures and core/shell structures. In some embodiments, the HNPs comprise semiconducting materials selected from Group II-VI semiconductors, alloys thereof and core/shell structures made therefrom. In further embodiments, the Group II-VI semiconductors are CdSe, CdS, CdTe, ZnSe, ZnS, ZnTe, alloys thereof, combinations thereof and core/shell, core multi-shell layered-structures thereof.

The metal/metal alloy materials are typically transition metals. Non-limiting examples of such are Cu, Ag, Au, Pt, Co, Pd, Ni, Ru, Rh, Mn, Cr, Fe, Ti, Zn, Ir, W, Mo, and alloys thereof.

In some embodiments, the metal is Au, Pd, and Pt and alloys thereof.

In further embodiments, the metal is Au, Pd, and Pt and alloys thereof and said at least one semiconductor material is CdS, CdSe or CdTe.

As stated above, the HNPs population may have a relatively narrow size distribution, namely they are manufactured or collected in a relatively narrow range of sizes. In fact, the standard deviation (sigma) of the particles' size in a single population may be less than 25%. In some embodiments, the deviation in the particles size is less than 15%. Where the nanoparticles are elongated (nanorods) the sigma of the length of a single population may be less than 35% and the sigma of the width is less than 15%. In some embodiments, the population of nanoparticles is homogenous in that said population comprises nanoparticles of relatively the same size and/or shape.

For certain applications it may be desirable to vary not only the size and shape of the HNPs, making up the population, but also the chemical composition of the nanoparticles and/or the arrangement of the semiconductor and metal/metal alloy regions along the nanoparticles. Thus, in some embodiments, the population of HNPs is a blend of one or more of the following types/groups of nanoparticles: HNPs of a certain pre-determined size distribution; HNPs of a certain pre-determined shape; HNPs having one metal/metal alloy region and one semiconductor region (optionally having one or more sub-region of different semiconducting materials); HNPs having at least two metal/metal alloy regions and a single semiconductor region (optionally having one or more sub-region of different semiconducting materials); HNPs having one metal/metal alloy region and at least two semiconductor region (optionally having each one or more sub-region of different semiconducting materials); HNPs having at least two metal/metal alloy regions and at least two semiconductor regions (optionally having one or more sub-region of different semiconducting materials), HNPs having at least two metal/metal alloy regions and at least two semiconductor regions (optionally having one or more sub-region of different semiconducting materials), wherein the arrangement (sequence) of regions or sub-regions along the nanostructure differs from one population to another; HNPs which may be photoactivated at only a particular wavelength or at a only predetermined wavelength or range of wavelengths; HNPs which do not undergo photoactivation as described herein.

The population of HNPs may be attained by mixing together one or more of the above types of nanoparticles. Alternatively, heterogeneous populations may be prepared by employing, e.g., non-stoichiometric amounts of starting materials. Each group of HNPs may be manufactured separately and stored for future use. As a person skilled in the art would realize, each of the above groups of HNPs may be prepared in a substantially uniform or homogenous fashion. However, due to random defects having to do with e.g., the manufacture process, purity of starting materials and other factors, a certain degree of HNPs having defects in size, shape, chemical composition, and other parameters, may be found in each of these types of HNPs. It should be noted that the presence of such defects does not necessarily reflect on any one of the herein disclosed characteristics.

A population of HNPs may comprise a blend of HNPs of one or more of the above types, in a known pre-determined ratio of nanoparticles or comprise a random mixture of such HNPs. In a certain non-limiting example, a population of HNPs comprises HNPs having a large variety of sizes and shapes, constructed of a single metal/metal alloy region and two semiconductor regions (optionally having one or more sub-region of different semiconducting materials). In another example, a population of HNPs may comprise HNPs of different shapes and different chemical compositions. In yet another example, the population comprises a blend of nanorods having at least one metal/metal alloy region at one or both ends of the elongated structure and/or at least one metal/metal alloy region in a central, non-terminal part of the elongated HNPs.

In addition, HNPs populations comprising any one nanoparticle according to the invention or employed in any one method of the invention, and at least one type of particle outside of the scope of the present application are also provided herein. Such mixed populations of HNPs herein described and HNPs known in the art may have advantageous effects suitable for any one application disclosed herein.

As will be discussed further below, by having the ability to provide blends of different HNPs populations it is possible to tune the optical properties of the material, thus utilizing the whole range of wavelengths efficiently. Alternations in the metal composition and size allow the fine-tuning of the Fermi level energy and the redox potential of the HNPs. The different shapes enable better control and the design of a great variety of devices.

EXPERIMENTAL DESCRIPTION

Chemicals: Trioctylphosphine (TOP, Sigma Aldrich, 90%) was vacuum distilled before use and stored under inert atmosphere. All other chemicals were used as purchased: cadmium oxide (>99.99%), trioctylphosphine oxide (TOPO, 99%), 1-octadecene (ODE, technical grade, 90%), oleic acid (95%), octadecylamine (ODA, ≥99%), didodecyldimethylammonium bromide (DDAB, 98%) and Gold(III)chloride (99%), Gold nanoparticles (5 nm diameter stabilized suspension in citrate buffer), L-glutathione reduced (GSH, ≥98.0%), Poly(styrene-co-maleic anhydride), cumene terminated (PSMA), sodium sulfide nonahydrate (≥98.0%), sodium sulfite (>98%), Polyethylenimine (PEI, branched average Mw~25,000), 4-aminoantipyrine (4-AAP, ≥98.0%), Superoxide dismutase from bovine erythrocytes (BioUltra, lyophilized powder, ≥4,500 units/mg protein, ≥97%), phenol (≥99.5%), terephthalic acid (TPA, 98%), 5,5-dimethyl-1-pyrroline-N-oxide (DMPO) were purchased from Sigma Aldrich. Oleylamine (technical grade, 90%) was purchased from Across. Octadecylphosphonic acid (ODPA) and hexylphosphonic acid (HPA) were purchased from PCI Synthesis. Sulfur (>99.0%) was purchased from Merck.

Synthesis of CdSe Seeds:

CdO (0.12 g), trioctylphosphine oxide (TOPO; 6.0 g) and octadecylphosphonic acid (ODPA; 0.56 g) were mixed in a 100 mL three-neck flask. The mixture was heated to 100° C. and placed under vacuum for 1 hour followed by three times of argon purging. Under argon atmosphere, the solution was heated to 300° C. to dissolve the CdO, forming a clear colorless solution. At this temperature, 1.8 mL of TOP was injected into the hot solution. Next, the solution was further heated to 350° C., at which 0.87 mL of precursor solution of selenium (0.21 g) in TOP (1.7 mL), was rapidly injected into the hot solution. The reaction time was, typically, 25 sec for CdSe seeds with diameter of ~2.3 nm. The reaction was quenched by removing the heating mantle and cooling with fan. The crude reaction mixture was diluted with toluene. Methanol was added in order to precipitate the nanocrystals and remove excess surfactants.

Figure 3:
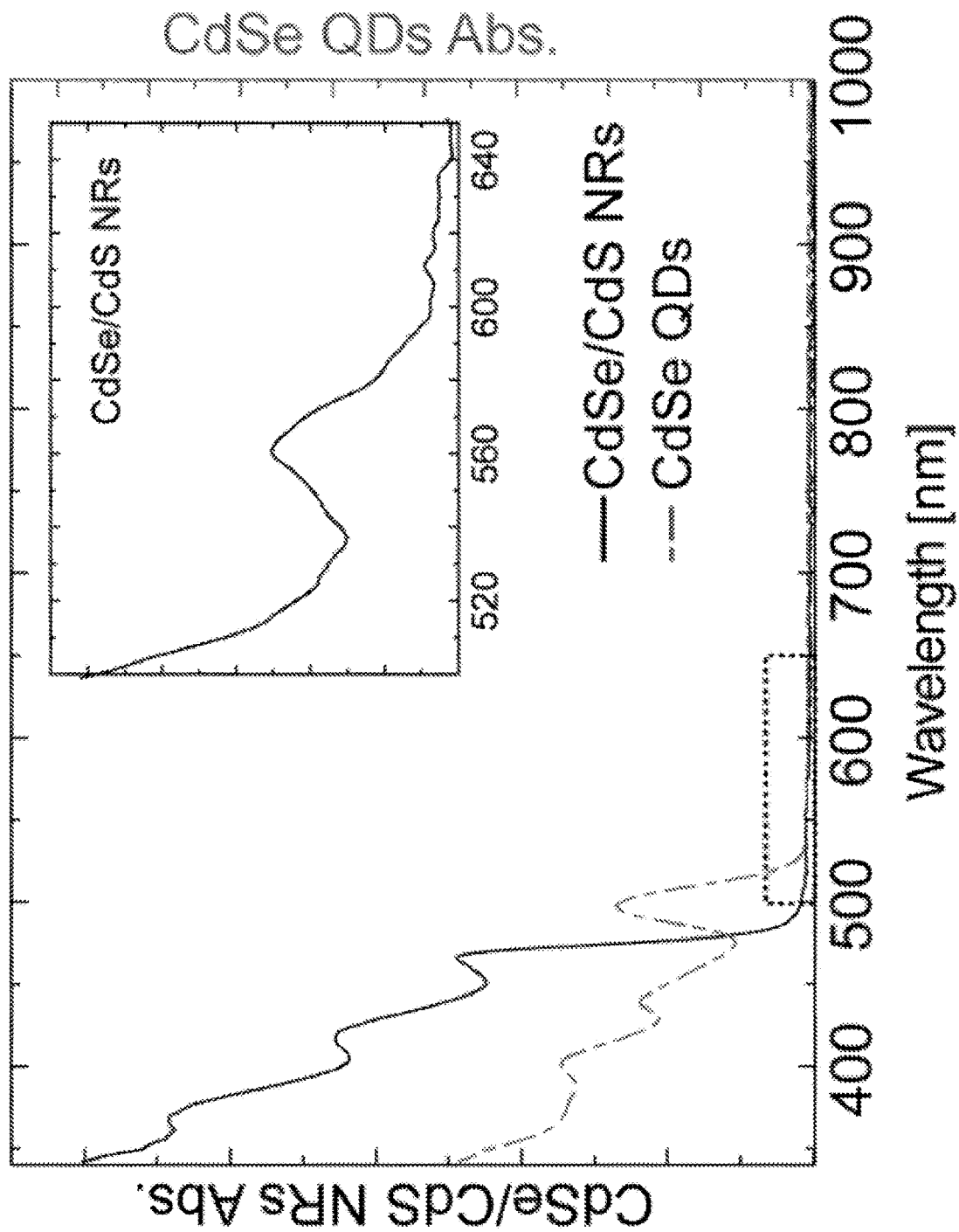
FIG. 3 provides absorption spectra of CdSe QDs and CdSe/CdS NRs. Inset showing the CdSe seed feature within the seeded rod structure.

Synthesis of Seeded CdSe/CdS Nanorods:

CdO (0.065 g), trioctylphosphine oxide (TOPO; 3.0 g), octadecylphosphonic acid (ODPA; 0.29 g) and hexylphosphonic acid (HPA; 0.065 g) were mixed in a 100 mL three-neck flask. The mixture was heated to 100° C. and placed under vacuum for 1 hour followed by three times of argon purging. Under argon atmosphere, the solution was heated to 300° C. and at this temperature 1.8 mL TOP was injected into the hot solution. Next, the solution was further heated to 360° C., at which a precursor solution of CdSe seeds (typically, $4 \times 10^{-8}$ mol) with sulfur in TOP solution (1.6 mL; 0.075 g/mL) was rapidly injected. The temperature decreased and then recovered within 1-2 min. The reaction time was, typically, 12 min. The reaction was quenched by removing the heating mantle and cooling with fan. The crude reaction mixture was diluted with toluene. Methanol was added in order to precipitate the nanocrystals and remove excess surfactants. Absorption spectra of both CdSe seeds and CdSe/CdS nanorods (NRs) are presented in Supplementary FIG. 3 including the CdSe seeds feature within the seeded rod structure (inset).

Synthesis of CdS Seeds:

CdS nanocrystal seeds were synthesized by a modification of a previously reported procedure. Cadmium oxide (CdO; 0.106 g), oleic acid (OA; 2.26 g) and 1-octadecene (ODE; 20 g) were mixed in a 100 mL three-neck flask. The mixture was heated to 100° C. and placed under vacuum for 1 hour followed by three times of argon purging. Under argon atmosphere, the solution was heated to 260° C. to dissolve the CdO, forming a clear colorless solution. A precursor solution consisting of sulfur (0.013 g) and ODE (7 mL) was rapidly injected into the hot solution. The reaction time was typically 90 sec for CdS seeds with diameter of ~3.1 nm. The reaction was quenched by removing the heating mantle and cooling with fan. The crude reaction mixture was precipitated with acetone followed by centrifugation. For further purification, the particles were dissolved in toluene and the precipitation procedure was repeated several times.

Synthesis of CdS Nanorods:

CdS nanorods were synthesized by a modification of a previously reported procedure employing seeded growth. CdO (0.12 g), trioctylphosphine oxide (TOPO; 6.0 g), octadecylphosphonic acid (ODPA; 0.68 g) and hexylphosphonic acid (HPA; 0.04 g) were mixed in a 100 mL three-neck flask. The mixture was heated to 100° C. and placed under vacuum for 1 hour followed by three times of argon purging. Under argon atmosphere, the solution was heated to 350° C. and at this temperature trioctylphosphine (TOP; 1.8 mL) was injected into the hot solution. Next, the solution was further heated to 365° C., at which a precursor solution of CdS seeds (typically, $3 \times 10^{-8}$ mol) and sulfur in TOP solution (1.6 mL; 0.075 g/mL) was rapidly injected into the hot solution. The temperature decreased and then recovered within 1-2 min. The reaction time was 9 min for 49 nm×4.2 nm CdS rods. The reaction was quenched by removing the heating mantle and cooling with fan. The crude reaction mixture was diluted with toluene. Methanol was added in order to precipitate the nanocrystals and remove excess surfactants.

Synthesis of CdS—Au and CdSe/CdS—Au Hybrid Nanorods:

A precursor stock solution consisting of octadecylamine (ODA; 0.055 g), didodecylammonium bromide (DDAB; 0.021 g) and AuCl$_3$ (0.010 g) in toluene (10 mL) was sonicated for 15 min to dissolve the AuCl$_3$, and the solution changes color from dark brown to yellow. In order to achieve selective growth of 1.5-1.8 nm gold tips on one apex of the NRs, a molar ratio of 700-900 Au ions per NR was used depending on the specific properties of the rods. Diluted Au growth stock solution was added to NRs (typically ~$2 \times 10^{-9}$ mol) in toluene (20 mL) in 100 mL flask under flowing argon. The solutions are mixed for 1 hour at room temperature and under dark conditions. The product hybrid nanoparticles (HNPs) are then washed and precipitated with acetone followed by separation via centrifugation. The hybrid samples had narrow size distribution according to their absorption spectra and TEM characterization measurements and statistics (FIG. 2).

Synthesis of ZnSe—Au:

ZnSe frames were synthesized by previously described synthesis [Jia et al., Nature Materials, 13, 301-307, (2014)]. Following purification by precipitation with methanol, For Au growth, ZnSe frames were dissolved in toluene and furthered mixed for ten minutes at room temperature with a degassed solution containing AuCl$_3$ and oleylamine.

Nanoparticle Characterization:

TEM characterization was performed using a Tecnai T12 G2 Spirit and Tecnai F20 G2. All size statistics are done with "Scion image" program on 200 particles. Absorption was measured with a JASCO V-570 UV-vis-near IR spectrophotometer. Extinction coefficient values of the NRs were calculated using a previously reported method.

Phase Transfer:

NPs were transferred to water by ligand exchange and polymer coating methods. For exchanging the native organic-soluble ligands with the thiolate alkyl ligands, the ligand exchange strategy was used. Stock solution of L-glutathione (GSH) was prepared by dissolving GSH (140 mg) and KOH (100 mg) in methanol (1 mL). Next, 200 µL of stock solution is added to NPs in chloroform (1 mL) with an optical density of 1.5 at the CdS first state transition and mixed for 1-2 min. Based TDW (pH 11-12) is added to the flocculated solution and after mixing phase separation appears and the NPs are extracted from the upper water phase after mild centrifugation.

Polymer coating was done with different polymers. Poly (styrene-co-maleic anhydride) (PSMA) coating is achieved by mixing 2 mL of nanoparticles solution with PSMA (20 mg) in chloroform (1 mL) for 5 hours. Then ethanolamine (20 µL) is added to the solution and mixed for 1-2 min. Next, recurring additions of TDW (1 mL) is done to transfer the particles to the above water phase followed by mild centrifugation before extraction. Polymer coating with polyethylenimine (PEI) was done by mixing NPs solution (1 mL) with PEI (0.15 g; MW 25,000) in chloroform (1 mL) for 1 hour. Then the particles are precipitated and washed with cyclohexane (1:1 chloroform/cyclohexane), followed by centrifugation. TDW is added to the precipitate and residues of PEI are removed by centrifugation.

Before use, all nanoparticle solutions were washed through 100 KDa cellulose membrane, to remove excess of polymer and ligands.

Figure 4A:
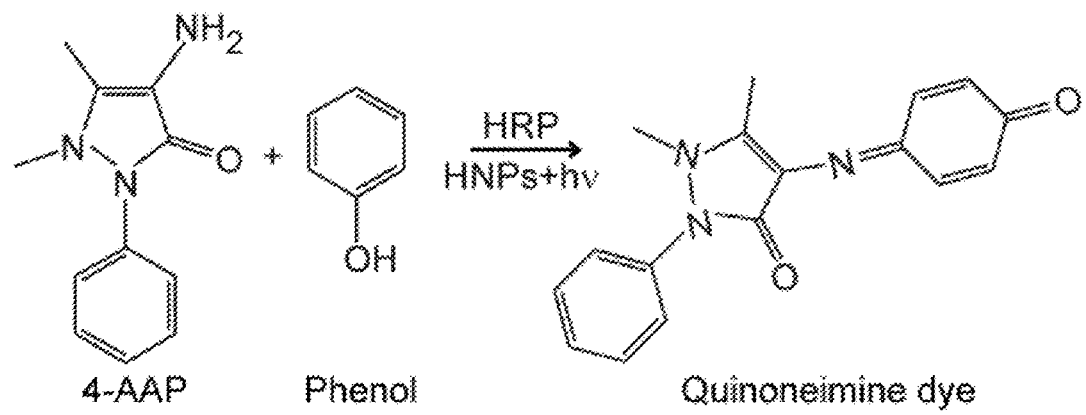
FIGS. 4A-B provide.

HRP Activity Assay:

The catalytic activity of the enzyme was measured spectroscopically following the change in the absorption spectrum due to the production of quinoneimine dye by HRP, as illustrated in FIG. 4A. Typically, 20 µL (1 mg/2.5 mL) HRP and 25 µL (1 mg/mL) SOD, 200 µL (8.125 mg/l mL) 4-aminoantipyrine (4-AAP), 600 µL (79 mg/mL) phenol and 100 µL of 10-100 nM HNPs/NPs were dissolved and mixed with PBS (final volume 2 mL). Then samples were irradiated using 405 nm laser (20 mW/cm$^2$) while measuring absorption.

Indoxyl acetate assay.

The cholinesterases activity was measured as follows. Typically, indoxylacetate was dissolved in PBS (1 mg/mL) and filtered with a 0.22 µm filter. A cuvette was filled with at least 50 µL of cholinesterase recombinant enzyme solution, enzymes conjugated to nanoparticles or serum. Then the cuvette was irradiated at 405 nm with a 20 mW laser for 7.5 minutes and two minutes after turning it off, 1 mL of indoxylacetate was injected to the cuvette. The kinetics of enzymatic activity was measured by detecting the emission of the product at 473 nm.

Figure 4B:
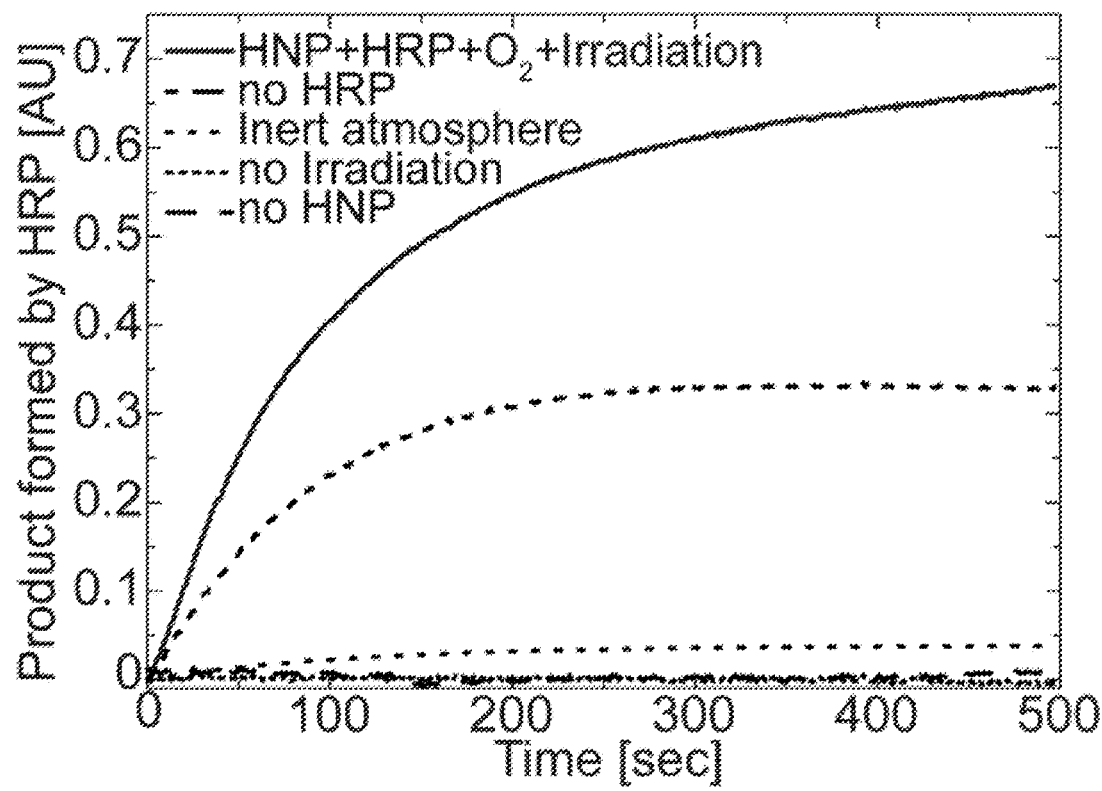

Control Experiments for the Photo-Switched HRP Activation:

Control measurements under various conditions were done in order to isolate the light induced HRP activation by NPs excitation from the intrinsic enzyme activity, or non-specific effects of the light excitation. As shown in FIG. 4B, inert atmosphere e.g. absence of oxygen, absence of HNPs or without irradiation, all show negligible activity and product formation in comparison to the product formation under the presence of the formers. This confirms their key role in the formation of the product. Unspecific product formation was also measured in the absence of enzyme. This false-positive signal could be attributed to phenol oxidation by presence of ROS following light irradiation. Note that the phenol oxidation is not mediated through direct charge transfer from the nanoparticles given the absence of this response under inert conditions. Therefore, in order to obtain the effective net contribution of the HNPs to the HRP activation, we subtracted this signal from all data and figures, presented in this frame of work.

Figure 6:
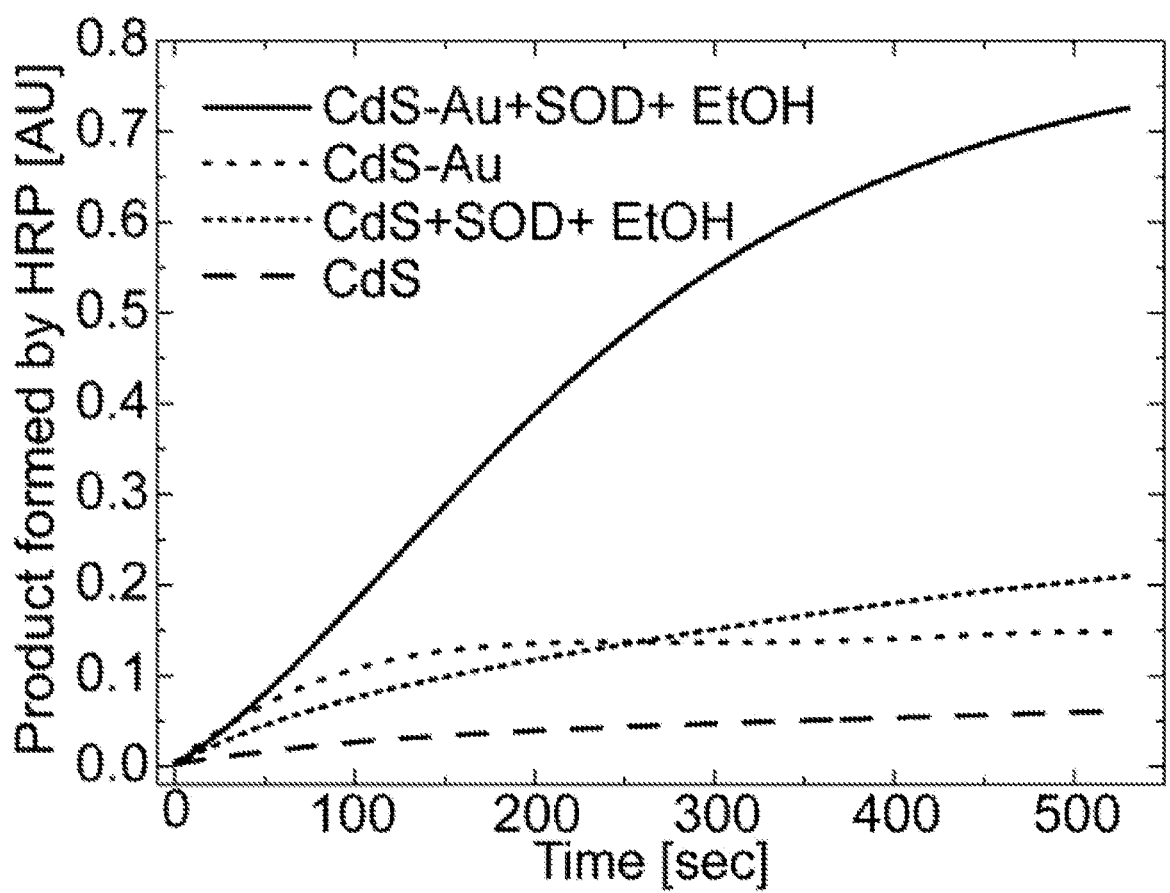
FIG. 6 shows comparison of HRP activity upon light irradiation between CdS—Au HNPs and CdS NRs in the presence of SOD and hole scavenger (e.g., EtOH) and in the absence of these additives.
Figure 7B:
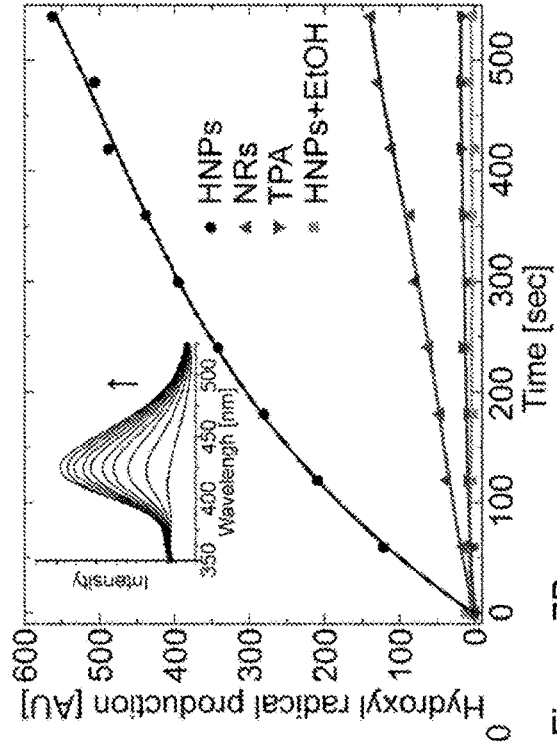
FIGS. 7A-D show HNPs photocatalytic ROS formation mechanism.
Figure 7A:
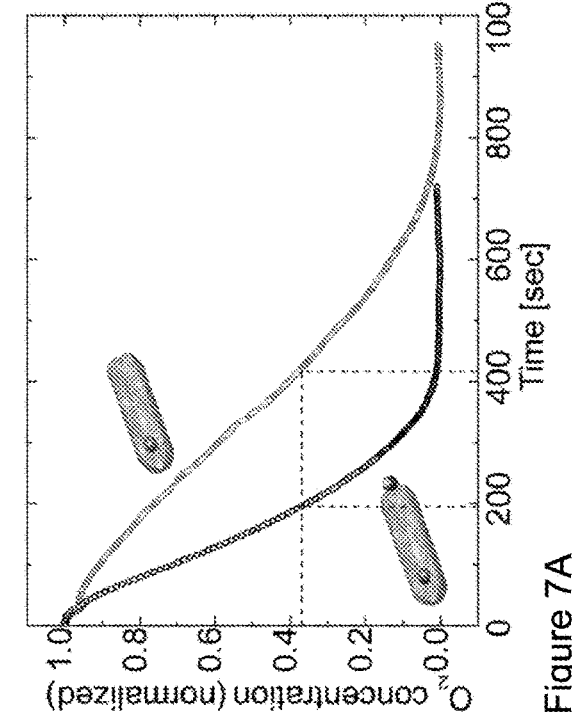
Figure 7D:
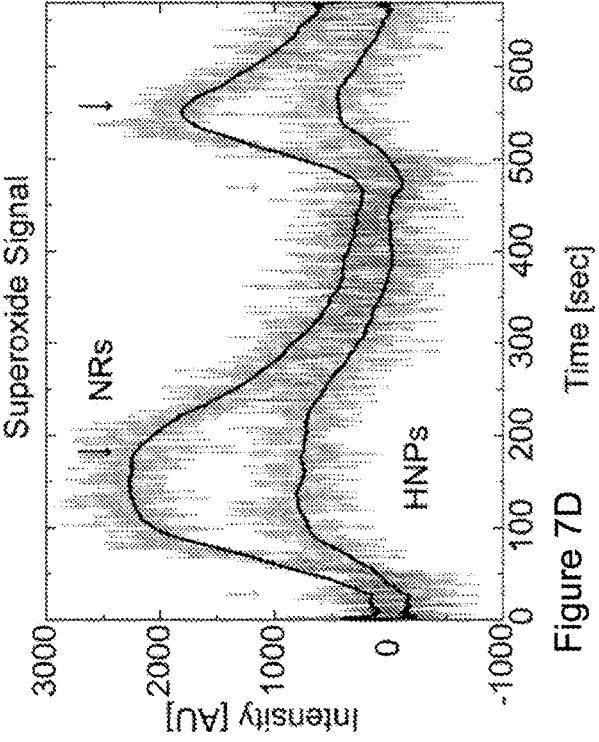
Figure 7C:
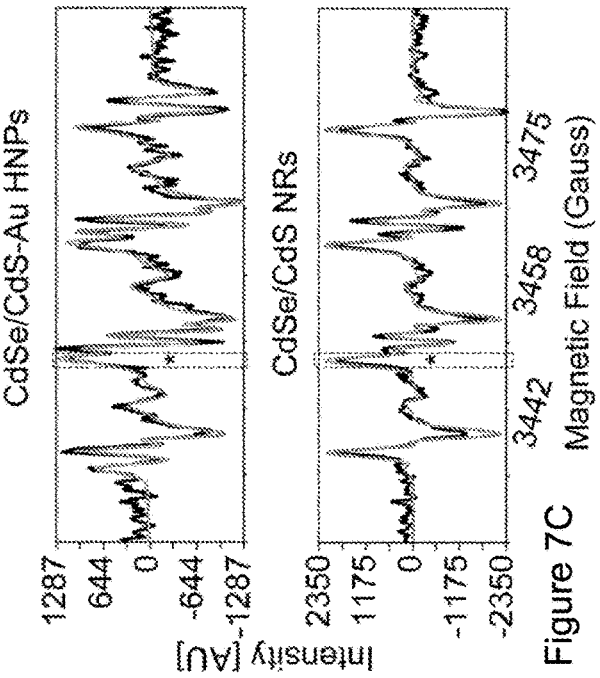

CdS—Au HNPs Show Higher Light Induced HRP Activation than CdS NRs:

The photo-induced activity of HRP was also investigated with CdS based nanosystem as photocatalysts. Comparison between CdS—Au HNPs and CdS NRs showed similar trends to those reported in the main manuscript for CdSe/CdS based nanosystem. As shown in FIG. 6, in all conditions, native and in the presence of SOD and hole scavenger (e.g. EtOH), the hybrid system reveals higher catalytic function and efficiency than the semiconductor alone. In addition, the effects of the hole scavenger and the presence of SOD enzyme on the overall HRP activity are repeated in this system as was demonstrated for the CdSe/CdS based systems. The contribution of each of the additives, SOD and EtOH is discussed in detail within the main manuscript.

Hydroxyl Radical Detection:

TPA in PBS (1340 μL, 0.236 mg/mL) was mixed with NPs (100 μL, ~60 nM) and PBS was added for a total volume of 2 mL. Samples were irradiated using 405 nm laser (20 mW/cm$^2$) and emission was measured with a Cary Eclipse Fluorometer (Varian Inc.), every minute after excitation at 310±5 nm.

Electron Paramagnetic Resonance (EPR):

ROS were detected by EPR spin-trapping technique coupled with 5,5-Dimethyl-1-pyrroline N-oxide (DMPO) as the spin trap molecule. DMPO was purified in double distilled water, with activated charcoal in the dark. After 15-30 minutes, the DMPO solution was filtered and its concentration was determined spectrophotometrically, using $\varepsilon_{277\ nm}=8000$ M$^{-1}$ cm$^{-1}$. The solution was stored at 20° C. for no longer than 2 weeks. Samples containing aqueous suspensions of nanoparticles and DMPO (10 mM) were drawn by a syringe into a gas-permeable Teflon capillary (Zeus Industries, Raritan, N.J.) and inserted into a narrow quartz tube that was open at both ends. Then, the tube was placed into the EPR cavity (ER 4102ST) and spectra were recorded, using Bruker EPR 100d X-band spectrometer, during or after illumination with 405 nm 20 mW/cm$^2$ laser. The EPR measurement conditions were as follows: frequency: 9.77 GHz; microwave power: 20 mW; scan width: 65G; center field: 3458G; resolution: 1024; receiver gain: 1×105; conversion time: 82 msec; time constant: 328 msec; sweep time: 84 sec; # scans=2; modulation amplitude: 2G; After acquisition, simulations of the recorded spectra were performed using an algorithm provided in the WINSIM program, which is available from NIEHS (National Institutes of Health, web site: http://epr.niehs.nih.gov/pest_mans/winsim.html). The results and simulation parameters used for analysis with comparison to relevant parameters reported from the literature are summarized in Table 1 and Table 2.

A time scan mode was used to follow on the increase in signal intensity upon in-situ illumination. The time measurements were taken at static magnetic field of 3448G, which fits the maximum of the second group of peaks from the low field, attributed to the DMPO adduct of superoxide radicals (DMPO-OOH). The parameters were similar to the field sweep mode except: conversion time: 328 msec; time constant: 328 msec; sweep time: 671 sec; # scans=1.

Figure 8:
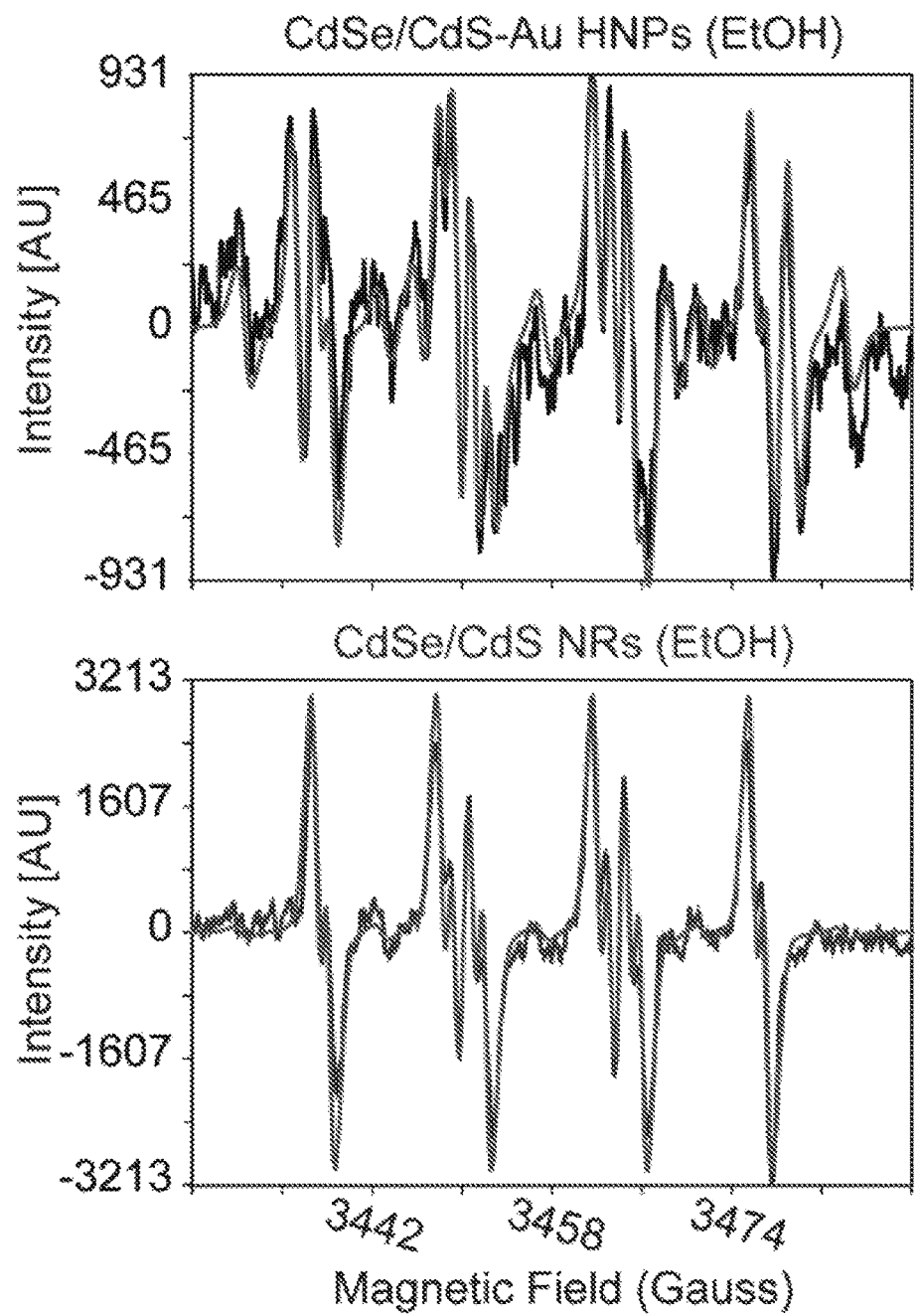
FIG. 8 shows EPR measurements during illumination of HNPs or NRs (upper and lower panels, respectively) in the presence of ethanol resulted in decreased signal of DMPO-OH and in increase in signal with hyperfine coupling of aN=15.8G and aH=22.8G which indicates the presence of $CH_3C^*HOH$, an ethanol-derived radical adduct. This confirms the DMPO-OH results from the presence of hydroxyl radicals in the solution.
Figure 9:
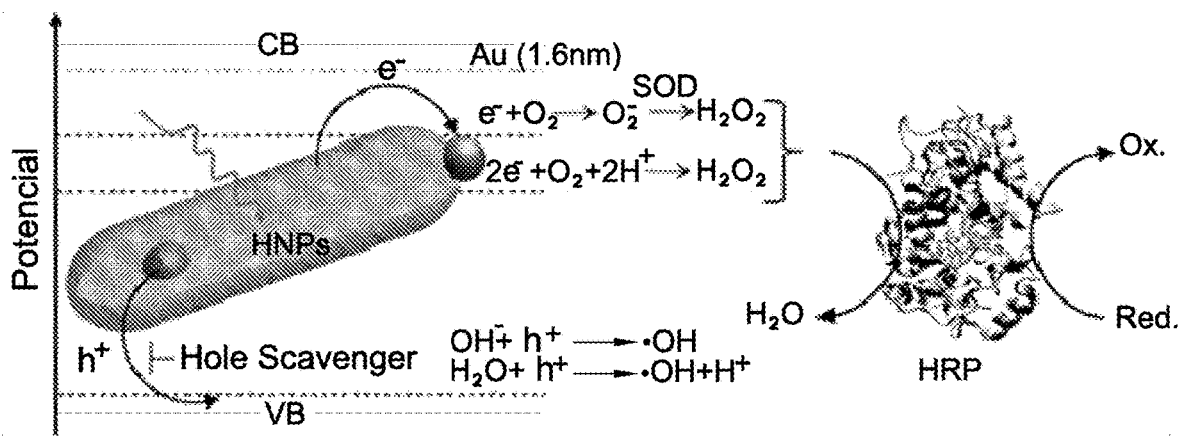
FIG. 9 provides a summary scheme showing the different pathways for ROS formation after HNP light activation, and their use for HRP modulation. Excitation of the semiconductor rods results in charge separation followed by reduction of molecular oxygen by the excited electrons. This results in direct formation of $H_2O_2$ that can be used as a substrate for HRP or in formation of superoxide that can be converted to $H_2O_2$ with the aid of SOD. In parallel, the holes can be used to produce hydroxyl radicals or could be scavenged by hole acceptors.
Figure 10A:
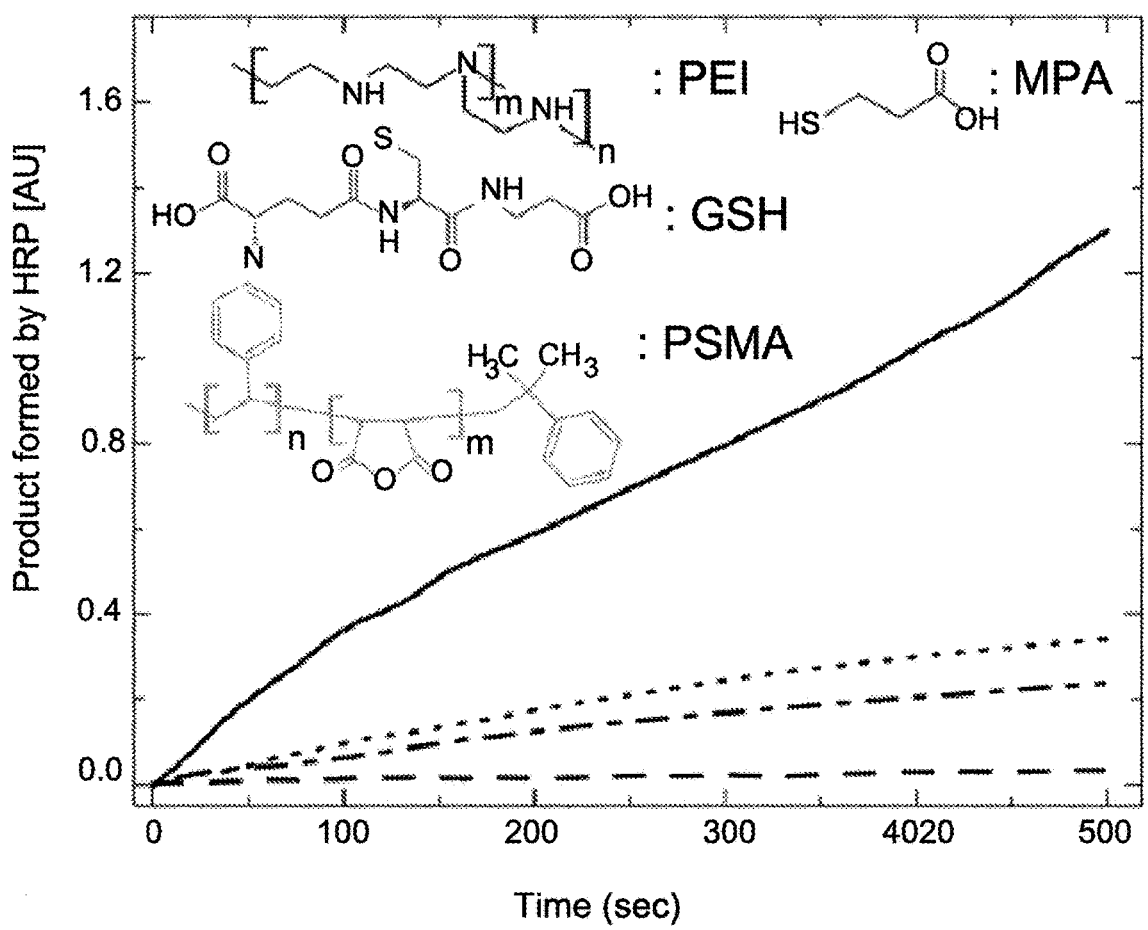
FIGS. 10A-C depict HNPs surface effects and biocompatibility properties.
Figure 10B:
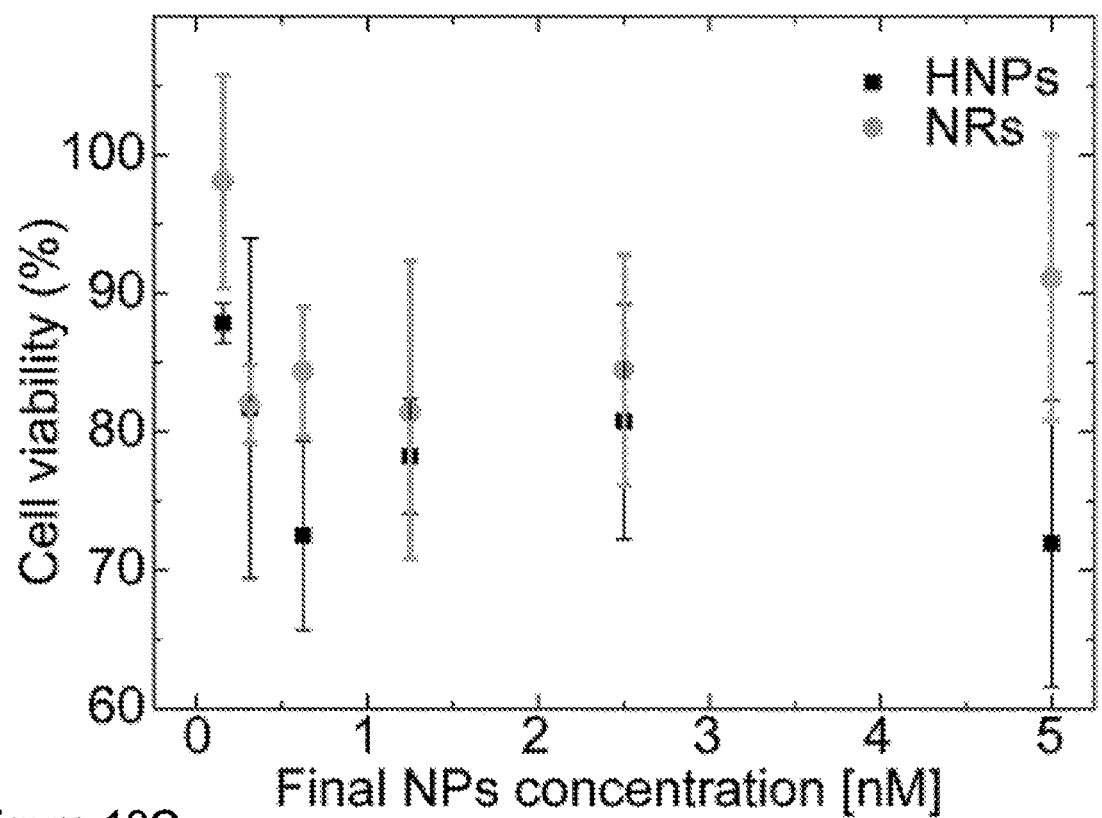
Figure 10C:
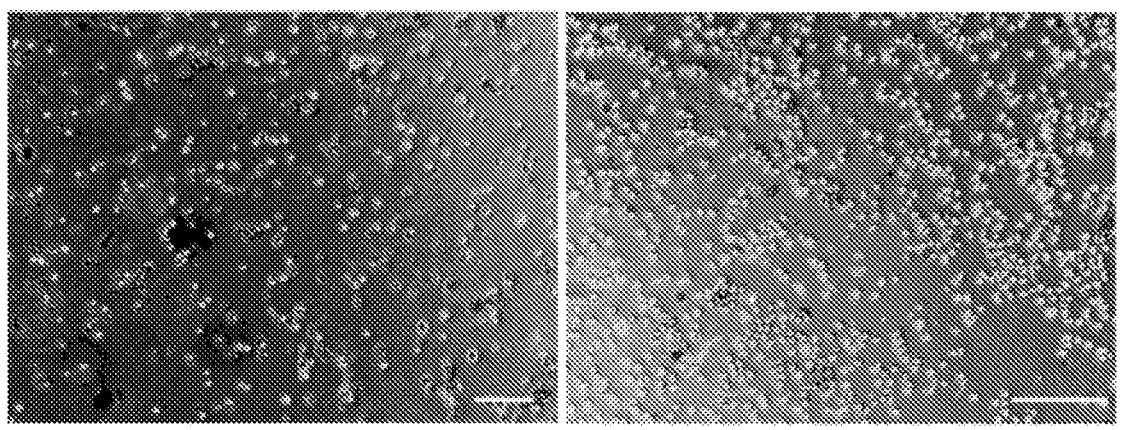
Figure 11A:
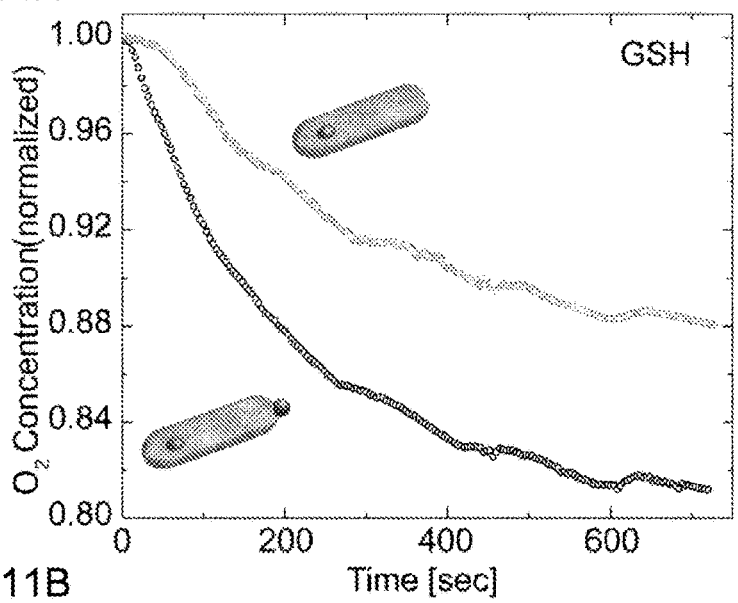
FIGS. 11A-C provide.
Figure 11B:
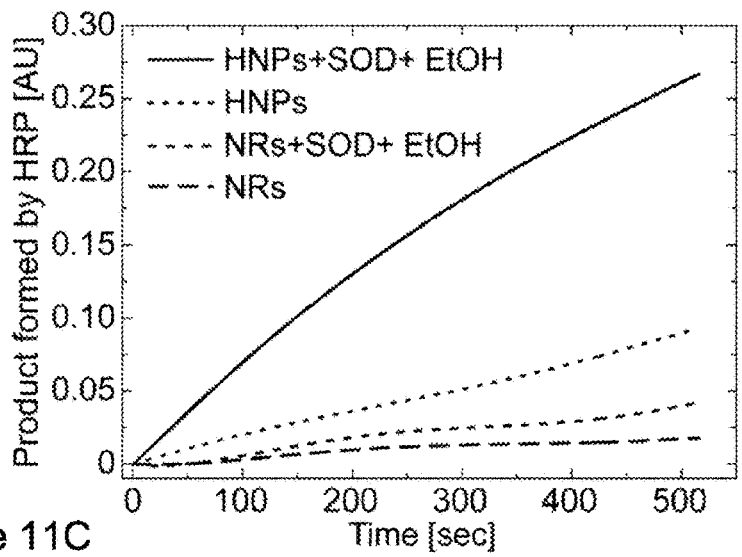
Figure 11C:
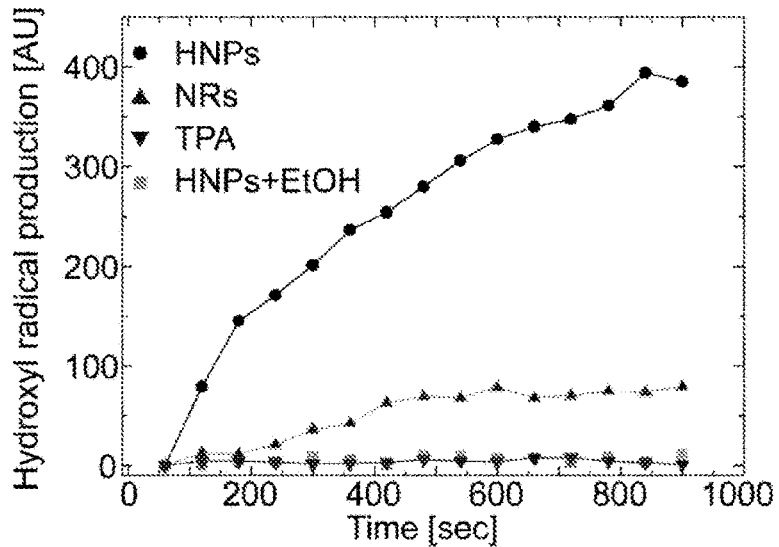
Figure 12A:
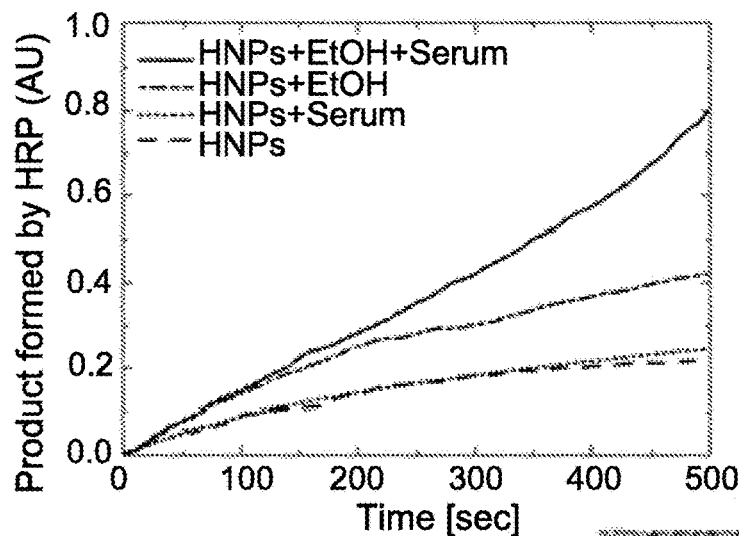
FIGS. 12A-C provide.
Figure 12B:
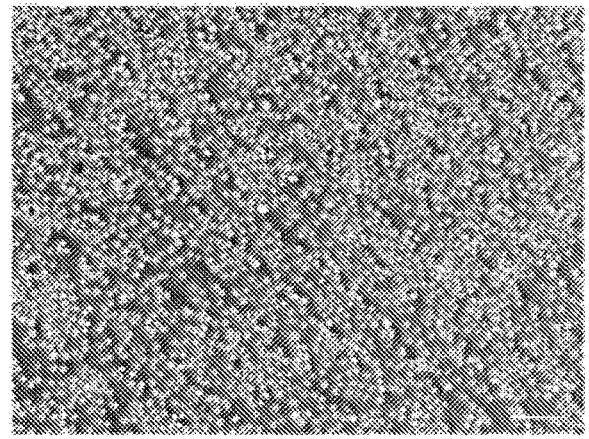
Figure 12C:
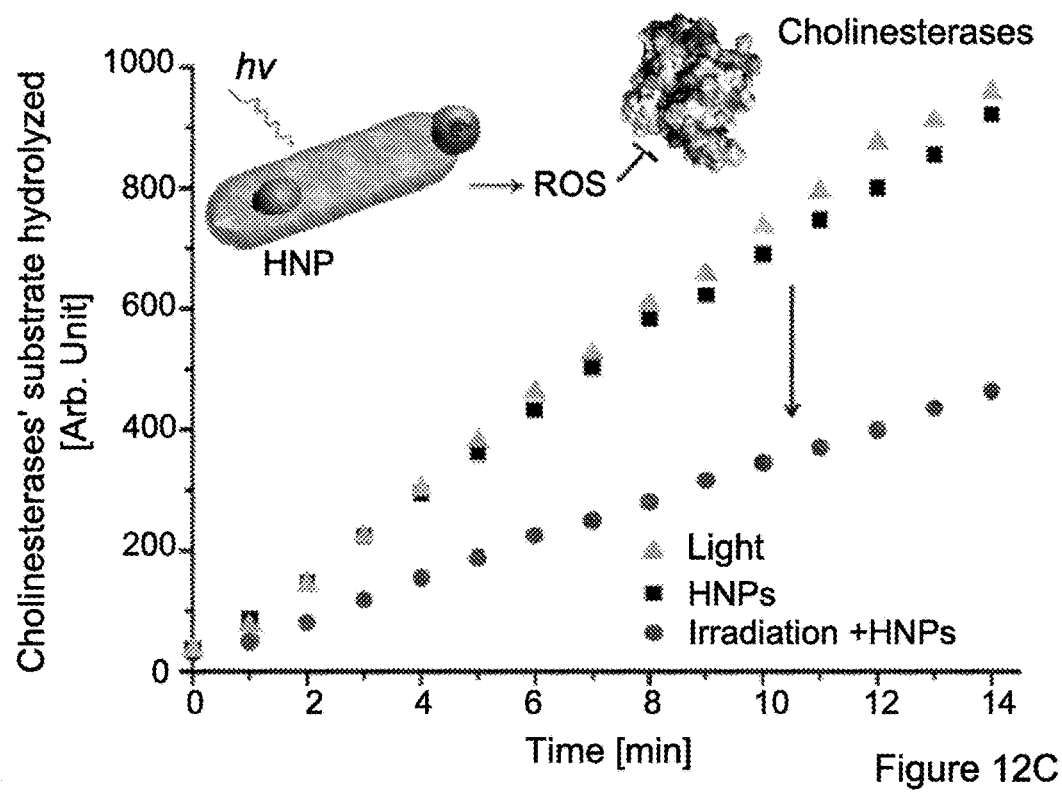
Figure 13:
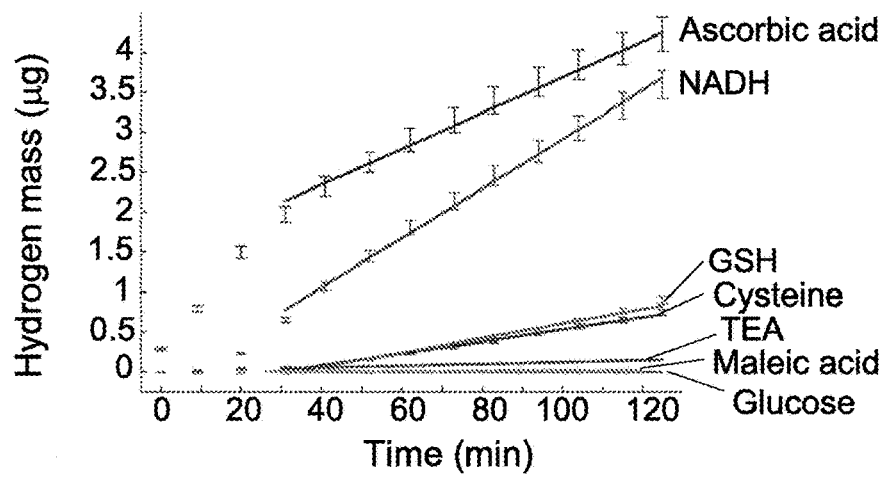
FIG. 13 shows kinetic measurements of hydrogen production with different biological molecules as hole acceptor agents in presence of CdS—Au HNPs (PEI coated).

Similar EPR experiments as were presented in the manuscript were also done in the presence of ethanol which can scavenge hydroxyl radicals (FIG. 8).

Oxygen Consumption Measurements:

Oxygen consumption was measured by polarography with a thermostatically controlled (37° C.) Clark oxygen electrode (Strathkelvin 782 Oxygen System; Strathkelvin Instrument Ltd.). HNPs/NRs with PEI and GSH surface coating with the typical concentrations of the HRP activity assay (100 μL of 10-100 nM) in PBS buffer solution were stirred in a closed cell. Under irradiation (405 nm laser 20 mW/cm$^2$) oxygen consumption was recorded for typically 10 min and calculated as rate of change in the oxygen concentration.

Glutathione as an Alternative Surface Coating:

As described in the phase transfer section above, both hybrids and semiconductor NPs were transferred to aqueous solutions with additional ligands including GSH via ligand exchange mechanism. The GSH coated systems were investigated for the photo-switched HRP activity under the same conditions as for PEI coated systems reported within the main manuscript. Similar behavior was observed for the GSH coated systems with regard to the trends shown for PEI surface coating.

Kinetic Photocatalytic Activity Measurements for HNPs with Different Biological Hole Acceptors:

In order to determine the photocatalytic activity of HNPs in the presence of different biological hole acceptors, hydrogen gas generation via the photocatalytic water reduction reaction was measured. The photocatalysts were dispersed in PBS solution (2 mL; optical density, OD~1 at 405 nm). The photocatalyst solution was placed in a quartz cuvette and hole scavengers (typically 0.05M), were added to the solution. The solution is purged with argon for 20 min and stirred to achieve oxygen free condition in which ROS formation is suppressed and hydrogen formation occurs. The HNPs were then illuminated with 405 nm 28 mW/cm$^2$ laser, producing 5.7×10$^{16}$ photons/sec. Aliquots of the reaction vessel head space were taken at different time intervals and the hydrogen was detected and quantified using Varian gas chromatograph (model 6820) equipped with a molecular sieve (5 Å) packed column and a thermal conductivity detector. The resulting chromatograms and hydrogen concentration are obtained by the comparison to a calibration curve of known hydrogen amounts.

Cell Culture:

K-562 human bone marrow cell line (ATCC® CCL-243™) were grown in 5% CO$_2$, 37° C. incubator in medium consisting of RPMI 1640 (Sigma, Cat# R0883) supplemented with 10% heat inactivated fetal bovine serum (Biological industries, Cat#04-121-1A), 1% L-glutamine (Biological industries, Cat#03-020-1A) and 1% penicillin and streptomycin (Gibco, Cat#15140-122). Cells were split every 3-4 days.

Biocompatibility:

The cytotoxic effects of the HNPs were assessed using Live/Dead assay and MTT viability test with K-562 cell line. Typically, cells were incubated with 10 μL of colloidal HNPs and CdSe/CdS nanorods solutions (1-100 nM) and 190 μL of cell medium in 96 well-plate. 21 hr after MTT was added to each well (0.25 mg/mL final concentration). Three hours after that, the cells were extracted by centrifugation at 3000 RPM for 5 min, cell's medium was replaced with DMSO and absorption was measured at 535 nm and 635 nm. The Live/Dead assay was performed 24 hr following the incubation with the NPs according to manufacturer instructions (molecular probes, Cat# L-7013). Working solution was made by diluting the Live/Dead dyes in HBSS buffer. The dye solution was added to the cell pellet followed by 15 minutes incubation in the dark. The cells were incubated for 15 minutes in 4% glutaraldehyde and then observed under fluorescent microscope. Similar Live/Dead assay was done 24 hr following illumination for 5 min with 405 nm 20 mW/cm² LED on the cells after their incubation for 1 hour with NRs or HNPs.

EXAMPLES

The following examples are non-limiting, and are provided as a demonstration of the concept of using photo-initiator catalysts in photo-polymerizable inks. The photo-initiator catalysts can be composed of a variety of elements, and their properties are tailored according to the intended application and the printing technology.

Example 1: CdS—Au Photo-Initiator and Measurement of Photo-Initiator Activity

CdS—Au hybrid nanoparticles were grown in a two-step process. In the first step CdS rods were synthesized by seeded growth approach yielding rods with diameters of 5 nm and length of 50 nm. In second step, Au was grown selectively on one apex of the CdS rod, yielding 2 nm sized Au tips. A ligand exchange procedure was applied, through coating by PEI (polyethyleneimine), to render the hybrid nanoparticles dispersible in water.

To determine the polymerization efficiency of nano-photoinitiator catalysts, polymerization kinetics of acrylamide in aqueous solutions with nano-photoinitiator catalysts was studied. Fourier Transform Infrared Spectrophotometer, (ALPHA FT-IR Spectrometer, Bruker) was used in conjunction with platinum ATR single reflection diamond accessory (Sample scans 30; Resolution 4 cm$^{-1}$). The polymerization medium comprised aqueous solutions of 15% w/w monomer (acrylamide) with cross-linking monomer polyethylene glycol 600 diacrylate (4% w/w) and nano-photoinitiator catalysts at various concentrations of 1E-7 M to 6E-7M. For comparison polymerization kinetics of aqueous acrylamide solutions with CdS—Au hybrid nanoparticles and CdS nanorods was also studied. Measurements were performed on ~15 µl of polymerization solution dropped on the ATR diamond. The UV light was radiated onto the sample through a chamber (at 2.5 cm height) centered at the ATR diamond. Monochromatic UV LED (Integration Technology, Oxfordshire, UK) irradiating at 385 nm was used for photo-curing. IR spectra were recorded after every 10 seconds, for a total duration of 180 seconds. The polymerization kinetics was studied by monitoring the FTIR spectra in the range of 1800-800 cm$^{-1}$.

The conversion of acrylamide was measured as decay of absorption peaks of methylene group vibrations at 988 cm$^{-1}$ (assigned to out-of-plane bending mode of the =C—H unit) normalized to the C=O stretching peak at 1654 cm$^{-1}$ as an internal standard (8). Area under the peak at 988 cm$^{-1}$ at different durations of UV exposure was compared with the sample with no UV exposure.

Figure 14A:
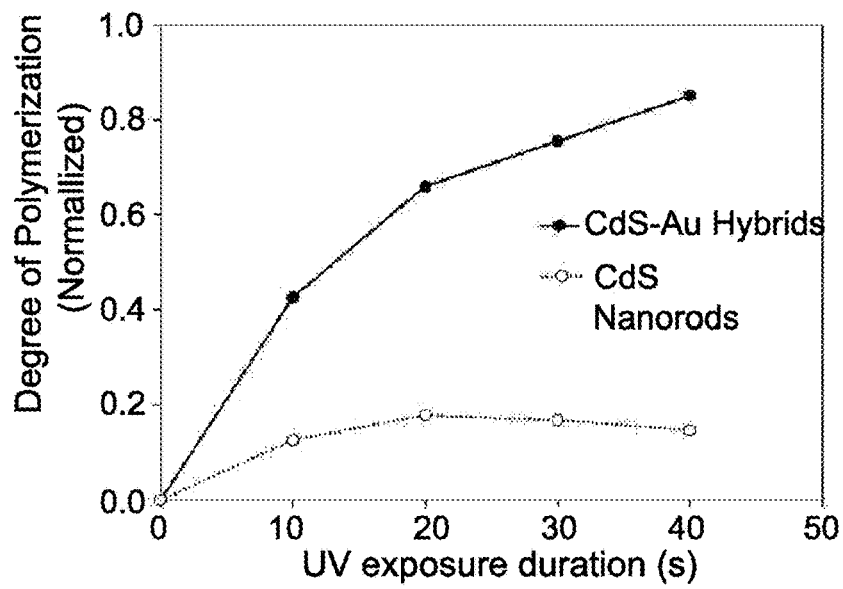

As shown in FIG. 14A, CdS—Au hybrid nanoparticles exhibit significantly faster polymerization than CdS nanorods. The difference between the polymerization kinetics by CdS—Au hybrid nanoparticles and CdS nanorods is statistically significant (t-test; $p<0.05$).

Figure 14B:
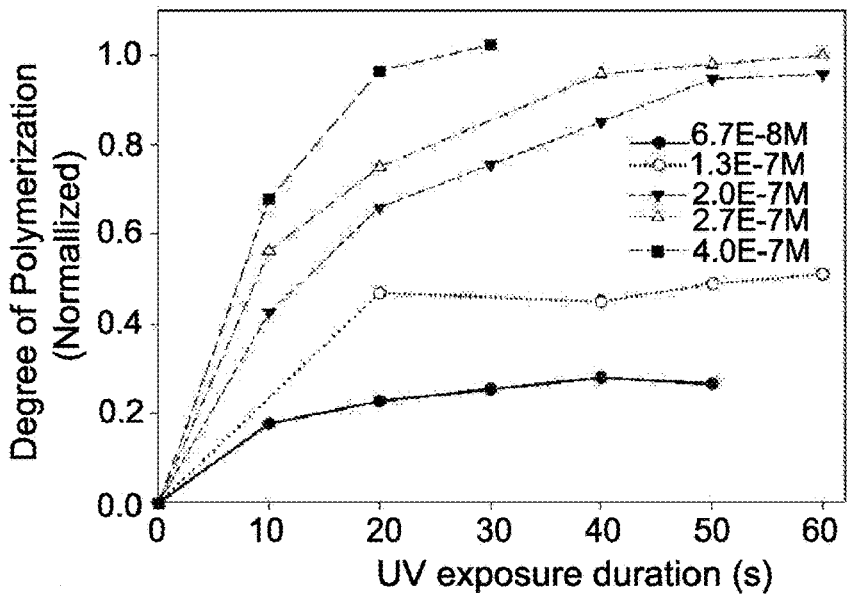

FIG. 14B shows effect of concentration of CdS—Au hybrid nanoparticles on polymerization kinetics of aqueous acrylamide solutions. Degree of polymerization is proportional to the concentration of CdS—Au hybrid nanoparticles. The nano-photoinitiator catalysts enabled much faster photopolymerization of acrylamide efficiently at concentrations of $6\times10^{-7}$ M.

Furthermore, to study the effect of irradiation wavelength, the degree of polymerization of aqueous acrylamide solutions containing CdS—Au hybrid nanoparticles ($4\times10^{-7}$M) at different excitation wavelengths 385 nm, 405 nm and 450 nm was measured and compared (FIG. 14C). The light intensity of all excitation sources was 25 mW/cm². The polymerization is applied at a wide range of wavelengths from the UV to the visible spectra, correlating with the absorbance feature of the CdS—Au. The CdS—Au hybrid nanoparticles showed high degree of polymerization with both UV and visible irradiations.

Example 2: 3D Printing of Model Hydrogel Using Photo-Curable Ink

Preparation of UV Curable Ink Formulation
Composition A:
Weigh 20 g of PEGylated diacrylate 600 (SR610). Add 80 g aqueous solution containing hybrid CdS—Au nanorods stabilized with PEI at concentration of 6-7M. Stir the solution to obtain a clear solution.
Composition B:
Weigh 40 g of PEGylated diacrylate 600 (SR610). Add 60 g aqueous solution containing hybrid CdS—Au nanorods stabilized with PEI at concentration of $6\times10^{-7}$M. Stir the solution to obtain a clear solution.
Composition C:
Weigh 25 g of Acrylamide and 25 g of PEGylated diacrylate 600 (SR610) together. Add 50 g aqueous solution containing hybrid CdS—Au nanorods stabilized with PEI at concentration of 6-7M and 5 g of aqueous solution containing CdSe—CdS nanorods. Stir the solution to obtain a clear solution.
Composition D:
Weigh 20 g of N-vinyl 2-pyrrolidone, 2 g sodium dodecyl sulfate and 2 g of PEGylated diacrylate 600 (SR610) together. Add 60 g aqueous solution containing hybrid CdS—Au nanorods stabilized with PEI at concentration of 6-7M. Stir the solution to obtain a clear solution.
Composition E:
Weigh 20 g of N-vinyl caprolactam with 2 g sodium dodecyl sulfate and 2 g of PEGylated diacrylate 600 (SR610) together. Add 60 g aqueous solution containing hybrid CdS—Au nanorods stabilized with PEI at concentration of 6-7M. Stir the solution to obtain a clear solution.
Composition F:
Weigh 20 g of N-Isopropylacrylamide with 2 g sodium dodecyl sulfate and 2 g of PEGylated diacrylate 600 (SR610) together. Add 60 g aqueous solution containing hybrid CdS—Au nanorods stabilized with PEI at concentration of 6-7M. Stir the solution to obtain a clear solution.
Composition G:
Weigh 30 g of 3-acryloxypropyl trimethoxysilane with 2 g sodium dodecyl sulfate and 3 g of PEGylated diacrylate 600 (SR610) together. Add 70 g aqueous solution containing hybrid CdS—Au Nanorods stabilized with PEI at concentration of 6-7M. Stir the solution to obtain a clear solution.

Composition H:

Weigh 40 g of 2-acryloylamido-2-methyl-propane sulfonic acid and 4 g of PEGylated diacrylate 600 (SR610) together. Add 60 g aqueous solution containing hybrid CdS—Au Nanorods stabilized with PEI at concentration of 6-7M. Stir the solution at 30° C. to obtain a clear solution.

Composition I:

Weigh 30 g of Acrylic acid and 3 g of PEGylated diacrylate 600 (SR610) together. Add 70 g aqueous solution containing hybrid CdS—Au nanorods stabilized with PEI at concentration of 6-7M. Stir the solution to obtain a clear solution.

Composition J:

Weigh 25 g of 1,6-hexane diol diacrylate and 2.5 g of PEGylated diacrylate 600 (SR610) together. Add 50 g aqueous solution containing hybrid CdS—Au nanorods stabilized with PEI at concentration of 6-7M and 25 g of isopropanol. Stir the solution to obtain a clear solution. This composition can be used for printing dental composites and structures.

3D printer (Freeform Plus 39, Asiga, Australia) was used. This printer operates by top-down stereolithography system with digital mirror device and UV-LED light source (385 nm). UV curable ink compositions A-J were used separately for each printing. Using Asiga composer software and .STL file for design, printing command was given with settings shown in Table 3:

TABLE 3

Setting for a 3D printer used in accordance with the invention.

| Exposure Time per Layer* (s) | 5-180 |
|---|---|
| Burn-In Layers | 0-10 |
| Burn-In Exposure Time (s)* | 0-240 |
| Layer Thickness [mm]* | 0.025-1.00 |
| Light Intensity mW/cm$^2$ | 17.5 |

*These setting were optimized for each printing and structure requirements.

Stable structured hydrogels (FIG. 15) were built using nano-photoinitiator catalysts. Based on the composition used the printed hydrogels had 50-80 w/w water content. Using Composition, structures with complex geometries such as Bucky Ball C180 were 3D printed (FIG. 15). As shown in FIG. 15B, these 3D printed structures fluoresce (glow) under UV illumination (365 nm). Thus, based on these findings, the nano-photoinitator catalysts can be used for high performance photo-polymerization including 3D printing of aqueous systems. This is on top of other printing applications as mentioned above.

Photocatalyitic Activity of Self-Polymerized Semiconductor-Metal Hybrid Nanoparticles (HNPs)

As described, the enhanced photocatalytic function of HNPs to produce reactive oxygen species (ROS) allows the polymerization of hydrogel monomers under visible light irradiation. The HNPs superiority over semiconductor nanocrystals in such process has been extensively discussed in the former sections concerning the relevant of photocatalytic ROS production for modulating enzymatic activity. This advantage is pf high relevance for the photo-polymerization process also holds other advantages over molecular photo-initiators as well. Moreover, the well-known and reported photocatalytic properties of HNPs can be further exploited in the new HNPs-hydrogel matrix. Post polymerized HNPs initiators maintain their photocatalytic properties. Hence, the printed matrix containing the HNPs within the polymer can functionalize it while acting as a unique 3D photocatalyst system. Therefore, in some embodiments, such system can be utilized as photocatalytic membranes for performing redox reactions upon light activation for several applications including water purification or waste treatment.

As demonstration of this novel aspect shown is a photocatalytic dye reduction of methylene blue (MB) by 3D HNPs-hydrogel system as follow:

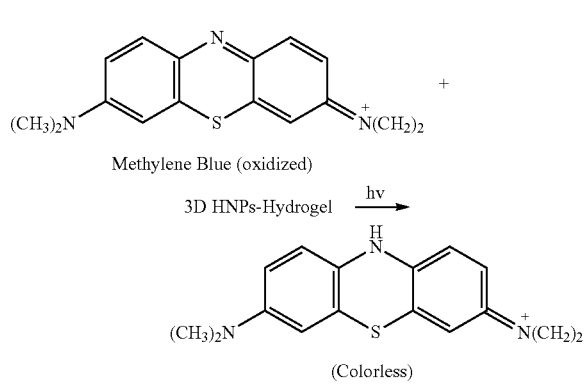

Figure 16:
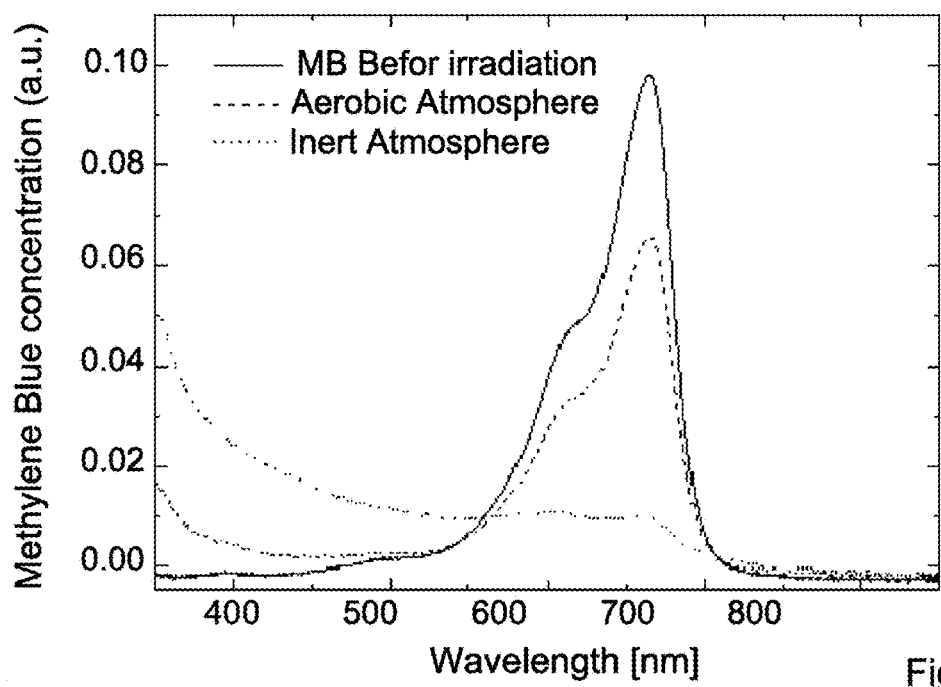
FIG. 16 demonstrates photocatalytic reduction of methylene blue (MB) by HNPs-hydrogel system. MB absorption before irradiation, reductant MB after 10 min of 405 nm illumination under aerobic and inert conditions. This provides an example for the use of HNPs as multi-functional material used both as photoinitiator and photocatalysts.

Already polymerized hydrogel with HNPs embedded in it as result of self-polymerization process under visible light illumination was inserted to a solution with MB dyes. Short (10 min) 405 nm irradiation resulted in MB reduction. This was done in ambient atmosphere as well as under inert condition, in both cases the MB was reduced, as shown in FIG. 16, however, under inert conditions the dye was fully reduced in comparison to partial MB reduction at aerobic environment. This photocatalytic activity could be mediated through the production of ROS or even through direct charge transfer of reductive excited electrons (in this case) from the fermi energy level of the metal to the reduction potential of the dye.

Figure 17A:
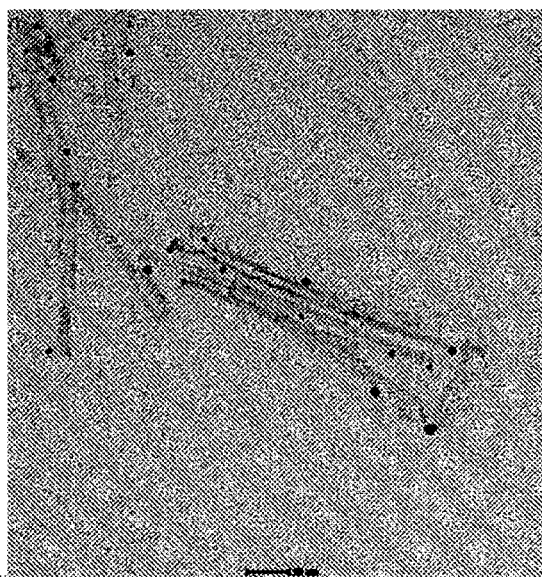
FIGS. 17A-C presents TEM images.
Figure 17B:
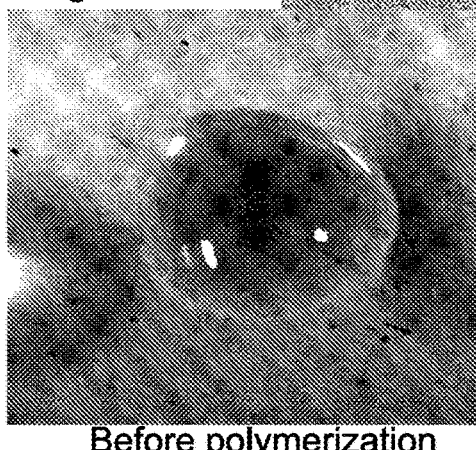
Figure 17C:
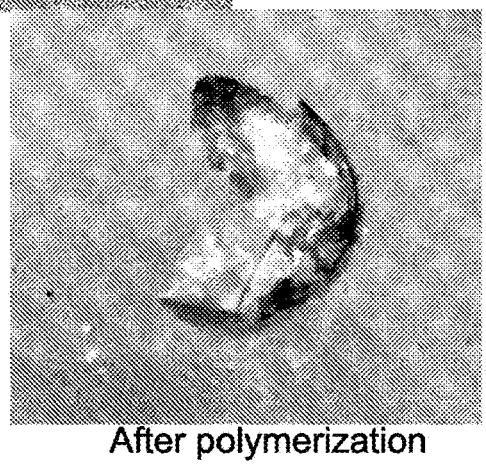

A non-limiting example of light-induced ROS formation and polymerization with cadmium free HNPs is provided in FIG. 17. It shows TEM image of ZnSe frames decorated with gold nanoparticles and images showing a polymerized matrix following light excitation of the HNPs.

The invention claimed is:

1. A method for generating a reactive species in the form of a radical or a peroxide in a medium, the process comprising irradiating a medium comprising hybrid nanoparticles (HNPs) and at least one polymerizable material susceptible of polymerization, wherein each of said HNP comprises at least one metal/metal alloy region and at least one semiconductor region.

2. The method according to claim 1, wherein the medium is a printed pattern.

3. The method according to claim 1, wherein said pattern is achieved by inkjet printing.

4. The method according to claim 3, wherein irradiation is carried out after, during, or concomitant with the patterning steps or after several layers have been deposited or after the full object has been formed.

5. The method according to claim 1, wherein the HNPs comprise at least two populations of nanoparticles, each population being reactive under light of a different wavelength.

6. The method according to claim 1, wherein the HNPs have at least one elongated structure element comprising a semiconductor material, bearing on at least one end portion thereof a material selected from metal and metal alloy.

7. The method according to claim 6, wherein semiconductor material is selected from Group II-VI semiconductors, Group III-V semiconductors, Group IV-VI semiconductors, Group IV semiconductors, Group III-VI semiconductors, Group I-VI semiconductors, ternary semiconductors, and alloys of any of the above semiconductors; or as combinations of the semiconductors in composite structures and core/shell structures.

8. The method according to claim 1, wherein the HNPs are in a form selected from dots, rods, platelets, tetrapods, frames, and nanodumbells, each form comprising at least one metal/metal alloy region and at least one semiconductor region.

9. The method according to claim 8, wherein the HNPs are nanodumbells.

10. The method according to claim 1, wherein the medium is a liquid or solid medium.

11. The method according to claim 10, wherein the medium is water or an aqueous medium.

12. The method according to claim 1, wherein the medium is a biological medium.

13. The method according to claim 10, wherein the solid medium is a solid object.

14. The method according to claim 1, for polymerizing at least one polymerizable material, the method comprising irradiating the medium comprising the HNPs and the at least one material susceptible of polymerization.

* * * * *